United States Patent [19]
Kuberasampath et al.

[11] Patent Number: 5,840,325
[45] Date of Patent: *Nov. 24, 1998

[54] OSTEOGENIC DEVICES

[75] Inventors: Thangavel Kuberasampath, Medway; David C. Rueger, West Roxbury, both of Mass.

[73] Assignee: Stryker Corporation, Kalamazoo, Mich.

[*] Notice: The term of this patent shall not extend beyond the expiration date of Pat. Nos. 5,108,753 and 5,011,691.

[21] Appl. No.: 606,839

[22] Filed: Feb. 26, 1996

Related U.S. Application Data

[63] Continuation of Ser. No. 268,252, Jun. 29, 1994, Pat. No. 5,496,552, which is a continuation of Ser. No. 103,604, Aug. 6, 1993, abandoned, which is a continuation of Ser. No. 827,052, Jan. 28, 1992, Pat. No. 5,250,302, which is a division of Ser. No. 579,865, Sep. 7, 1990, Pat. No. 5,108,753, which is a division of Ser. No. 179,406, Apr. 8, 1988, Pat. No. 4,968,590.

[51] Int. Cl.⁶ .................. A61F 13/00; A61F 2/00
[52] U.S. Cl. .................. 424/420; 424/422; 424/423; 424/424
[58] Field of Search ............ 424/420, 422, 424/423, 424

[56] References Cited

U.S. PATENT DOCUMENTS

| | | |
|---|---|---|
| 4,294,753 | 10/1981 | Urist. |
| 4,394,370 | 7/1983 | Jefferies. |
| 4,434,094 | 2/1984 | Seyedin et al.. |
| 4,455,256 | 6/1984 | Urist. |
| 4,563,350 | 1/1986 | Nathan et al.. |
| 4,563,489 | 1/1986 | Urist. |
| 4,877,864 | 10/1989 | Wang et al.. |
| 5,011,691 | 4/1991 | Oppermann et al. ......... 424/423 |
| 5,013,649 | 5/1991 | Wang et al.. |
| 5,108,753 | 4/1992 | Kuberasampath et al. ........ 424/422 |
| 5,496,552 | 3/1996 | Kuberasampath et al. ........ 424/4 |

FOREIGN PATENT DOCUMENTS

| | | |
|---|---|---|
| 0128041 | 12/1984 | European Pat. Off.. |
| 0148155 | 7/1985 | European Pat. Off.. |
| 0169016 | 1/1986 | European Pat. Off.. |
| 0212474 | 3/1987 | European Pat. Off.. |
| 0182483 | 5/1988 | European Pat. Off.. |
| WO85/05274 | 12/1985 | WIPO. |
| WO86/00526 | 1/1986 | WIPO. |
| WO88/00205 | 1/1988 | WIPO. |
| WO89/09605 | 10/1989 | WIPO. |
| WO89/10409 | 11/1989 | WIPO. |
| WO90/03733 | 4/1990 | WIPO. |

OTHER PUBLICATIONS

Canalis et al. (1980), "Stimulation of DNA and Collagen Synthesis by Autologous Growth Factor in Cultured Fetal Rat Calvaria," 210 *Science* 1021–1023.

Glowacki et al. (1981), "Application of the Biological Principle of Induced Osteogenesis For Craniofacial Defects," *The Lancet* 959–963.

Reddi, A.H. (1981), "Cell Biology and Biochemistry of Endochondral Bone Development," 1 *Coll. Res.* 209–226.

Sampath et al. (1981), "Dissociative Extraction and Reconstitution of Extracellular Matrix Compents Involved in Local Bone Differentiation," 78 *Proc. Natl. Acad. Sci. USA* 12:7599–7603.

Farley et al. (1982), "Human Skeletal Growth Factor: Characterization of the Mitogenic Effect on Bone Cells In Vitro," 21 *Biochemistry* 3508–3513.

Maugh, Thomas H. (1982) "Human Skeletal Growth Factor Isolated," 217 *Science* 819.

Sampath et al. (1983), "Homology of Bone–Inductive Proteins From Human, Monkey, Bovine, and Rat Extracellular Matrix," 80 *Proc. Natl. Acad. Sci. USA* 6591–6595.

Seyedin et al. (1983), "In Vitro Induction of Cartilage–Specific Macromolecules By A Bone Extract," 97 *J. Cell Biol.* 1950–1953.

Simpson, Ellen (1983), "Growth Factors Which Affect Bone," 9 *Trends. Biochem. Sci.* 527–530.

Urist et al. (1983), "Human Bone Morphogenetic Protein (hBMP)," 173 *Proc. Soc. Exper. Biol. & Med.* 194–199.

Urist et al. (1983), "β–Tricalcium Phosphate Delivery System For Bone Morphogenetic Protein," 187 *Clin. Orthop. Rel. Res.* 277–280.

Urist et al. (1984), "Purification of Bovine Bone Morphogenetic protein by Hydroxyapatite Chromatography," 81 *Proc. Natl. Acad. Sci. USA* 371–375.

Centrella et al. (1985), "Transforming and Nontransforming Growth Factors Are Present in Medium Conditioned By Feral Rat Calvariae," 82 *proc. Natl. Acad. Sci. USA* 7335–7339.

Klausner, Arthur (1985). "Collagen Corp. Isolates Cartilage Inducers," 3 *Biotechnology* 567–568.

Olson et al. (1985), "Deglycosylation of Chondroitin Sulfate Proteoglycan by Hydrogen Fluoride in Pyuidine," 146 *Anal. Biochem.* 232–237.

Reddi, A.H. (1985), "Implant–Stimulated Interface Reactions During Collagenous Bone Matrix–Induced Bone Formation," 19 *J. Biomed. Mat. Res.* 233–239.

Sampath et al. (1985), "Role of Extracellular Matrix Components in Cartilage and Bone Induction," Allen R. Liss, Publ., NY, pp. 412–428.

Seyedin et al. (1985), "Purification and Characterization of Two Cartilage–Inducing Factors From Bovine Demineralized Bone," 82 *Proc. Natl. Acad. Sci. USA* 2267–2271.

(List continued on next page.)

Primary Examiner—Nathan M. Nutter
Attorney, Agent, or Firm—Testa, Hurwitz & Thibeault, LLP

[57] ABSTRACT

Disclosed are osteogenic devices comprising a matrix containing substantially pure mammalian osteogenic protein and methods of inducing endochondral bone growth in mammals. A partial amino acid sequence, amino acid composition, solubility properties, and various other data characterizing osteogenic protein are also disclosed, as well as a nucleic acid sequences encoding a consensus osteogenic protein.

31 Claims, 15 Drawing Sheets

OTHER PUBLICATIONS

Colowicki et al., "Preparation and Bioassay of Bone Morphogenetic Protein and polypeptide Fragments," 146 *Meth. Enzymol.* 294–312.

Padgett et al. (1987), "A Transcript From a Drosophila Pattern Gene Predicts A Protein Homologous To The Transforming Growth Factor–βFamily," *Nature* 323:81–84.

Sampath et al. (1987), "Isolation of Osteogenin, An Extracellular Matrix–Associated Bone–Inductive Protein, By Heparin Affinity Chromatography," 84 *Proc. natl. Acad. Sci. USA* 7109–7113.

Weeks et al. (1987), "A Maternal mRNA Localized To The Vegetal Hemisphere in Xenopus Eggs Codes For A Growth Factor Related to TGF–β," 51 *Cell* 861–867.

LeGendre et al. (1988) "Direct Protein Microsequencing From Immobilon–P Transfer Membrane," 6 *BioTechniques* 2:154–159.

Wang et al. (1988), "Purification and Characterization of Other Distinct Bone–Inducing Factors," 85 *Proc. Natl. Acad. Sci. USA* 9484–9488.

Wang et al. (1988), "Purification and Characterization of Cartilage and Bone Inducing Factors," *Calcified Tissue International* 42 (Suppl.): A37 (Abstr. No. 146).

Wozney et al. (1988), "Identification Through Molecular Cloning of Factors Involved In Vivo Cartilage Formation," *Calcified Tissue International* 42 (Suppl.): A37 (Abstr. No. 147).

Wozney et al. (1988), "Novel Regulators of Bone Formation: Molecular Clones and Activities," 242 *Science* 1528–1534.

Lyons et al. (1989), "VGR–1, A Mammalian Gene Related to Xenopus Vg–1, is a Member of The Transforming Growth Factor β Gene Superfamily," 86 *Proc. Natl. Acad. Sci. USA* 4554–4558.

Wang et al. (1990), "Recombinant Human Bone Morphogenetic Protein Induces Bone Formation," 87 *Proc. Natl. Acad. Sci. USA* 2220–224.

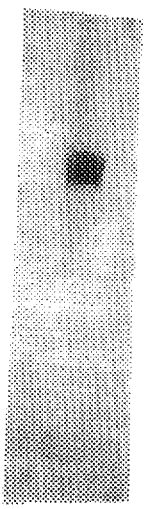 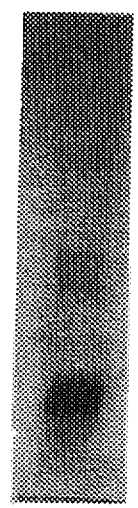
Fig. 3A   Fig. 3B
 
Fig. 4A   Fig. 4B

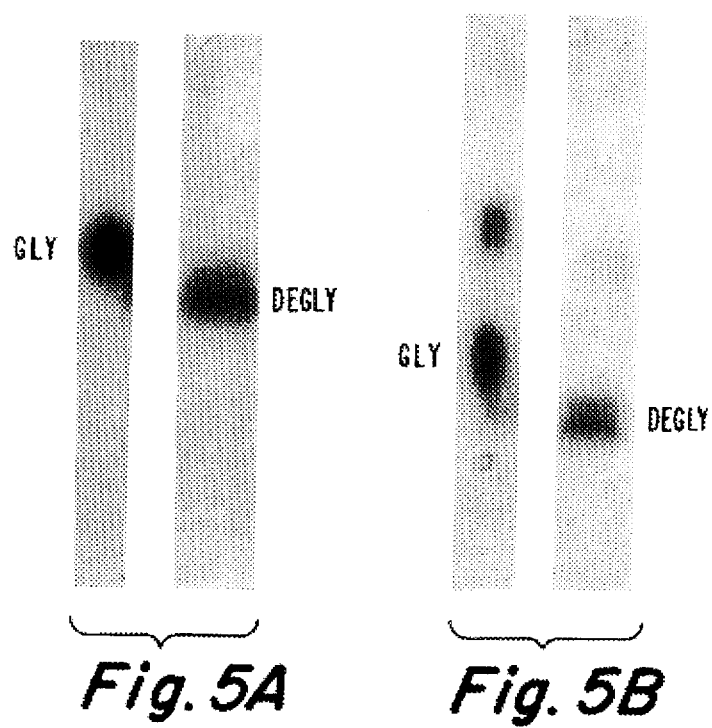

CONSENSUS GENE/PROBE:

```
          10         20         30         40
GATCCTAATGGGCTGTACGTGGACTTCCAGCGCGACGTGGGCTGGGAC
 D  P  N  G  L  Y  V  D  F  Q  R  D  V  G  W  D
Sau3A        RsaI                AccII
                                 HhaI 50         60         70         80         90
GACTGGATCATCGCCCCCGTCGACTTCGACGCCTACTACTGCTCCGGA
 D  W  I  I  A  P  V  D  F  D  A  Y  Y  C  S  G
    Sau3A         AccI   TaqI                BspMII
                  HincII AhaII               HpaII
                  SalI   HgaI+
                  TaqI 100        110        120        130        140
GCCTGCCAGTTCCCCTCTGCGGATCACTTCAACAGCACCAACCACGCCG
 A  C  Q  F  P  S  A  D  H  F  N  S  T  N  H  A
        MnlI+    Sau3A                        DraIII
                                              Pf1MI 150        160        170        180        190
TGGTGCAGACCCTGGTGAACAACATGAACCCCGGCAAGGTACCCAAGC
 V  V  Q  T  L  V  N  N  M  N  P  G  K  V  P  K
         EcoRII            HpaII    BanI
         HphI+             NciI    KpnI
         ScrFI             ScrFI   RsaI 200        210        220        230        240
CCTGCTGCGTGCCCACCGAGCTGTCCGCCATCAGCATGCTGTACCTGGA
 P  C  C  V  P  T  E  L  S  A  I  S  M  L  Y  L  D
    Fnu4HI         AluI            NspHI     EcoRII
                                   SphI      RsaI
                                             ScrFI 250        260        270        280        290
CGAGAATTCCACCGTGGTGCTGAAGAACTACCAGGAGATGACCGTGGT
 E  N  S  T  V  V  L  K  N  Y  Q  E  M  T  V  V
   EcoRI              MboII+  EcoRII
                              ScrFI 300        310
GGGCTGCGGCTGCCGCTAACTGCAG
cccgacgccgacggcgattgacgt
 G  C  G  C  R  *
 Fnu4HIFnu4HI
    Fnu4HIFnu4HI
```

Fig. 13

OSTEOGENIC DEVICES

This is a continuation of application Ser. No. 08/268,252 filed on Jun. 29, 1994 and now U.S. Pat. No. 5,496,552 which is a continuation of U.S. Ser. No. 08/103,604 filed Aug. 6, 1993, now abandoned and which is a continuation of U.S. Ser. No.07/827,052 filed Jan. 28, 1992 and now U.S. Pat. No. 5,250,302, which is a divisional of U.S. Ser. No. 07/579,865 filed Sep. 7, 1990 and now U.S. Pat. No. 5,108,753, which is a divisional of U.S. Ser. No. 07/179,406 filed Apr. 8, 1988 and now U.S. Pat. No. 4,968,590.

BACKGROUND OF THE INVENTION

This invention relates to osteogenic devices, to protein which can induce osteogenesis in, mammals, to a method of rapidly and reproducibly purifying osteogenic protein from mammalian bone, and to bone repair procedures using the osteogenic device.

Mammalian bone tissue is known to contain one or more proteinaceous materials, presumably active during growth and natural bone healing, which can induce a developmental cascade of cellular events resulting in endochondral bone formation. This active factor (or factors) has variously been referred to in the literature as bone morphogenetic or morphogenic protein, osteogenic bone inductive protein, or osteogenic protein, or osteogenin.

The developmental cascade of bone differentiation consists of chemotaxis of mesenchymal cells, proliferation of progenitor cells, differentiation of cartilage, vascular invasion, bone formation, remodeling, and finally marrow differentiation (Reddi, (1981) Collagen Rel. Res. 1:209–226).

Though the precise mechanisms underlying these phenotypic transformations are not clear, it has been shown that the natural endochondral bone differentiation activity of bone matrix can be dissociatively extracted and reconstituted with inactive residual collagenous matrix to-restore full bone induction activity (Sampath and Reddi, (1981) Proc. Natl. Acad. Sci. USA 78:7599–7603). This provides an experimental method for assaying protein extracts for their ability to induce endochondral bone in vivo.

This putative bone inductive protein has been shown to have a molecular mass of less than 50 kilodaltons (kD). Several species of mammals produce closely related protein as demonstrated by cross species implant experiments (Sampath and Reddi (1983) Proc. Natl. Acad. Sci. USA 80:6591–6595).

The potential utility of these proteins has been widely recognized. It is contemplated that the availability of the pure protein would revolutionize orthopedic medicine, certain types of plastic surgery, and various periodontal and craniofacial reconstructive procedures.

The observed properties of these protein fractions have induced an intense research effort in various laboratories directed to isolating and identifying the pure factor or factors responsible for osteogenic activity. The current state of the art of purification of osteogenic protein from mammalian bone is disclosed by Sampath et al. (Proc. Natl. Acad. Sci. USA (1987) 80). Urist et al. (Proc. Soc. Exp. Biol. Med. (1984) 173:194–199) disclose a human osteogenic protein fraction which was extracted from demineralized cortical bone by means of a calcium chloride-urea inorganic-organic solvent mixture, and retrieved by differential precipitation in guanidine-hydrochloride and preparative gel electrophoresis. The authors report that the protein fraction has an amino acid composition of an acidic polypeptide and a molecular weight in a range of 17–18 kD. This material was said to be distinct from a protein called "bone derived growth factor" disclosed by Canalis et al. (Science (1980), 210:1021–1023) and by Farley et al. (Biochem. (1982) 21:3508–3513).

Urist et al. (Proc. Natl. Acad. Sci. USA (1984) 81:371–375) disclose a bovine bone morphogenetic protein extract having the properties of an acidic polypeptide and a molecular weight of approximately 18 kD. The authors reported that the protein was present in a fraction separated by hydroxyapatite chromatography, and that it induced bone formation in mouse hindquarter muscle and bone regeneration in trephine defects in rat and dog skulls. Their method of obtaining the extract from bone results in ill defined and impure preparations.

European Patent Application Serial No. 148,155, published Oct. 7, 1985, purports to disclose osteogenic proteins derived from bovine, porcine, and human origin. One of the proteins, designated by the inventors as a P3 protein having a molecular weight of 22–24 kD, is said to have been purified to an essentially homogeneous state. This material is reported to induce bone formation when implanted into animals.

International Application No. PCT/087/01537, published Jan. 14, 1988, discloses an impure fraction from bovine bone which has bone induction qualities. The named applicants also disclose putative bone inductive factors produced by recombinant DNA techniques. Four DNA sequences were retrieved from human or bovine genomic or cDNA libraries and apparently expressed in recombinant host cells. While the applicants stated that the expressed proteins may be bone morphogenic proteins, bone induction was not demonstrated, suggesting that the recombinant proteins are not osteogenic. See also Urist et al., EP 0,212,474 entitled Bone Morphogenic Agents.

It is an object of this invention to provide osteogenic devices comprising matricies containing dispersed, substantially pure osteogenic protein. Another object is to provide a reproducible method of isolating osteogenic protein from mammalian bone tissue. Another object is to characterize the protein responsible for osteogenesis including the determination of molecular weight, amino acid sequence, quartenary structure, and presence of glycosylation. Another object is to provide substantially pure osteogenic protein capable of inducing endochondral bone formation in mammals, including humans. Yet another object is to provide genes encoding mammalian osteogenic protein and methods for their production using recombinant DNA techniques.

These and other objects and features of the invention will be apparent from the description, drawings, and claims which follow.

SUMMARY OF THE INVENTION

This invention involves osteogenic devices which, when implanted in a mammalian body, can induce at the locus of the implant the full developmental cascade of endochondral bone formation and bone marrow differentiation. The device comprises a carrier material having the characteristics disclosed below and substantially pure mammalian osteogenic protein. As used herein, the phrase "substantially pure" means free of other contaminating proteins having no endochondral bone formation activity.

The substantially pure osteogenic protein may include forms having varying glycosylation patterns, a family of related proteins having regions of amino acid sequence homology, and active truncated or mutated forms of native protein, no matter how derived. The osteogenic protein in its native form is glycosylated and has an apparent molecular weight of 30 kD as determined by SDS-PAGE; the deglycosylated protein has an apparent molecular weight of 27 kD. When reduced, the 30 kD protein gives rise to two glycosylated polypeptide chains having in the range apparent molecular weights of 16 kD and 18 kD; the deglycosylated polypeptides have molecular weights in the range of 14 kD to 16 kD. After reduction, osteogenic activity is absent. The osteogenic protein is further characterized by the approximate amino acid composition set forth below:

| Residue amino acid residue | Rel. # of Res./Molecule Rel. No. residues molecule | Residue amino acid residue | Rel. # of Res./Molecule Rel. No. residues molecule |
| --- | --- | --- | --- |
| Aspartic acid/ Asparagine | 22 | Tyrosine | 11 |
|  |  | Valine | 14 |
| Glutamic acid/ Glutamine | 24 | Methionine | 3 |
|  |  | Cysteine | 16 |
| Serine | 24 | Isoleucine | 15 |
| Glycine | 29 | Leucine | 15 |
| Histidine | 5 | Proline | 14 |
| Arginine | 13 | Phenylalanine | 7 |
| Threonine | 11 | Tryptophan | ND |
| Alanine | 18 |  |  |
| Lysine | 12 |  |  |

Analysis of digestion fragments indicate that the 30 kD osteogenic protein comprises the following amino sequences:

(1) D-F-D-A-Y-Y-C-S-G-A-C-Q-F-P-S;
(2) S-L-K-P-S-N-Y-A-T-I-Q-S-I-V;
(3) T-C-C-V-P-E-L-S-A-I-S-M-L-Y-L-D-E-N;
(4) M-S-S-L-S-I-L-F-F-D-E-N;
(5) S-Q-E-L-Y-V-D-F-Q-R;
(6) F-L-H-C-Q-F-S-E-R-N-S;
(7) T-V-G-Q-L-N-E-Q-S-S-E-P-N-I-Y; and
(8) I-Y-D-P-M-V-V.

The substantially pure osteogenic protein is useful in clinical applications only in conjunction with a suitable delivery or support system (matrix). The matrix is made up of particles or porous materials. The pores must be of a dimension to permit progenitor cell migration and subsequent differentiation and proliferation. The particle size should be within the range of 70–850 μm, preferably 70–420 μm. It may be fabricated by close packing particulate material into a shape spanning the bone defect, or by otherwise structuring as desired, a material that is biocompatible (non-inflammatory) and, biodegradable in vivo to serve as a "temporary scaffold" and substratum for recruitment of migratory progenitor cells, and as a base for their subsequent anchoring and proliferation. Useful matrix materials comprise collagen, homopolymers and copolymers of glycolic acid and lactic acid, hydroxyapatite, tricalcium phosphate and other calcium phosphates, and particulate, demineralized, guanidine extracted, species-specific (allogeneic) bone.

Availability of substantially pure osteogenic protein and of osteogenic devices will permit the physician to obtain optimal predictable bone formation to correct, for example, acquired and congenital craniofacial and other skeletal or dental anomalies (Glowacki et al. (1981) Lancet 1:959–963). The devices may be used to induce local endochondral bone formation in non-union fractures as demonstrated in animal tests, and in other clinical applications where bone formation is desirable.

In an important aspect of the invention, the availability of the protein in substantially pure form, and knowledge of its amino acid sequence and other structural features, permits the identification, cloning, and expression of genes which encodes osteogenic protein. Thus, in view of this disclosure, skilled genetic engineers can design and synthesize genes or isolate genes from cDNA or genomic libraries which encode appropriate amino acid sequences, and then express them in various types of host cells to produce large quantities of active proteins in native forms, truncated analogs, muteins, fusion proteins, and other constructs capable of inducing bone formation in mammals including humans.

BRIEF DESCRIPTION OF THE DRAWING

The foregoing and other objects of this invention, the various features thereof, as well as the invention itself, may be more fully understood from the following description, when read together with the accompanying drawings, in which:

FIGS. 3A and 3B are a photographic reproduction of a Coomassic blue stained SDS polyacrylamide gel of the osteogenic protein under non-reducing (A) and reducing (B) conditions;

FIGS. 4A and 4B are a photographic reproduction of a con A blot of an SDS polyacrylamide gel showing the carbohydrate component of oxidized (A) and reduced (B) 30 kD protein;

FIGS. 5A and 5B are photographic reproductions of an autoradiogram of an SDS polyacrylamide gel of $^{125}$I-labelled deglycosylated osteogenic protein under non-reducing (A) and reducing (B) conditions;

FIG. 13 is a schematic representation of the DNA sequence, restriction sites, and corresponding amino acid sequence of the consensus gene/probe for osteogenic protein.

DESCRIPTION

Figure 1A:
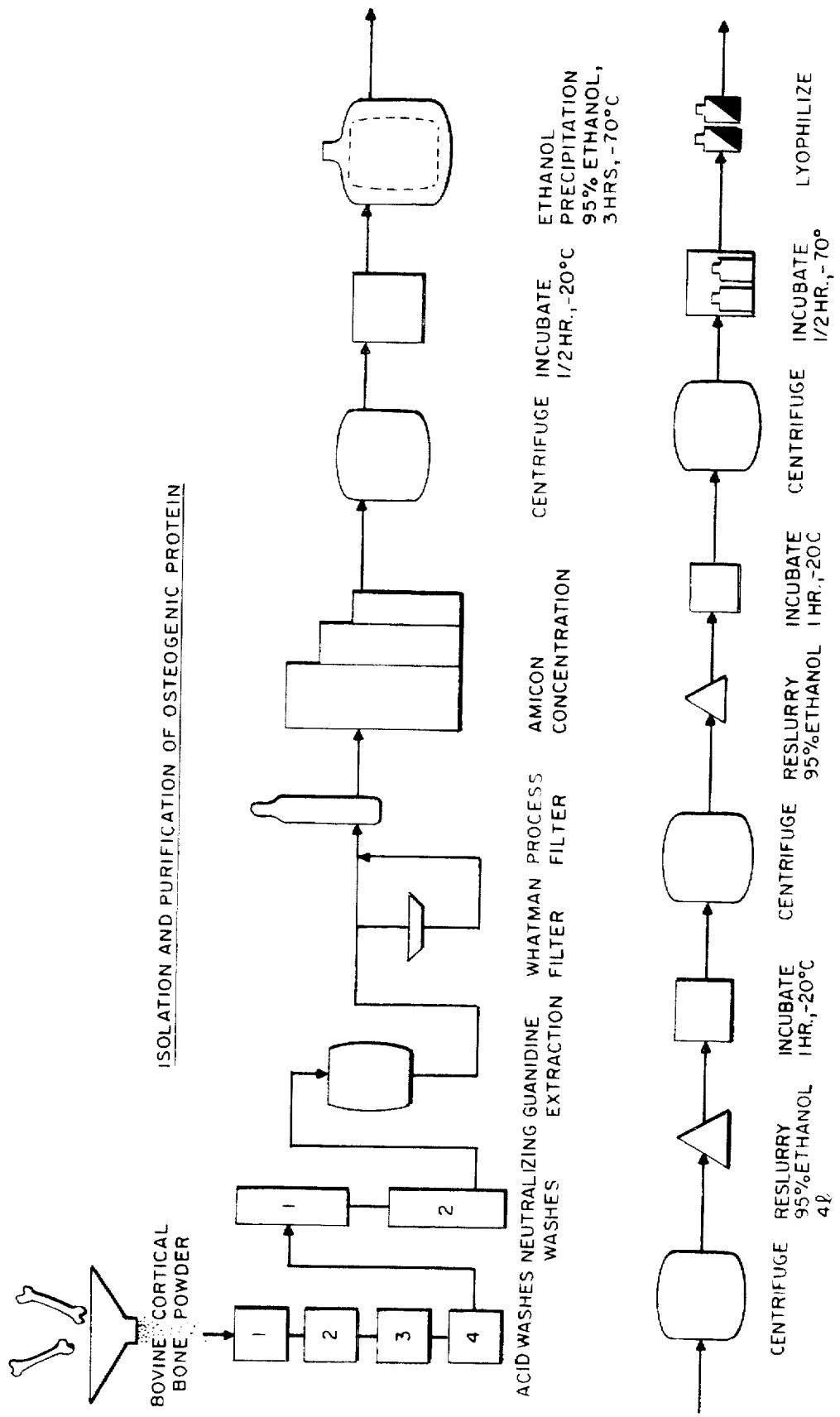
FIGS. 1A and 1B are a flow diagram of a purification procedure for isolating osteogenic protein.
Figure 1B:
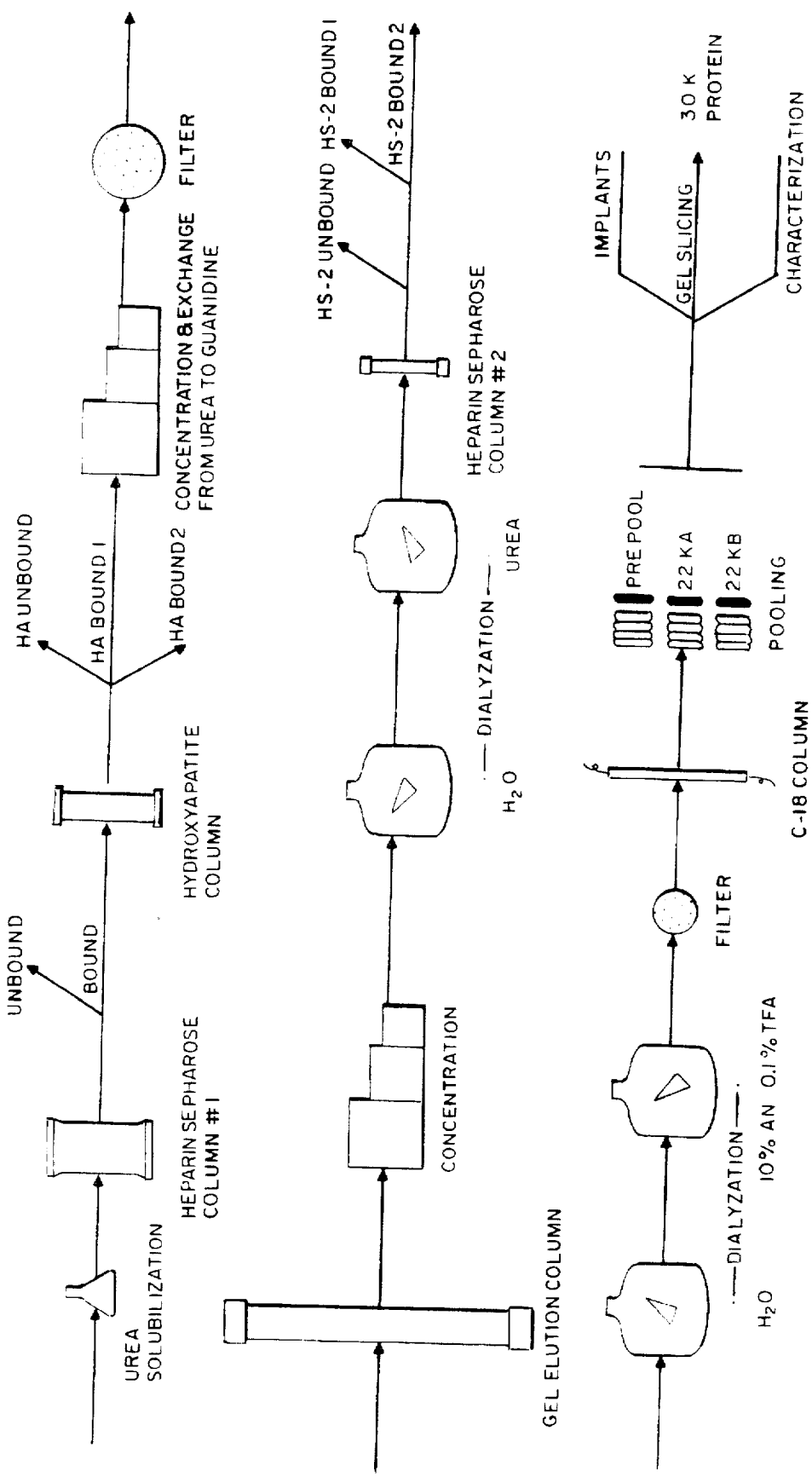

Purification protocols have been developed which enable isolation of the osteogenic protein present in crude protein extracts from mammalian bone. While each of the separation steps constitute known separation techniques, it has been discovered that the combination of a sequence of separations exploiting the protein's affinity for heparin and for hydroxyapatite (HAP) in the presence of a denaturant such as urea is key to isolating the pure protein from the crude extract. These critical separation steps are combined with separations on hydrophobic media and with gel exclusion chromatography.

The isolation procedure enables the production of significant quantities of substantially pure osteogenic protein from any mammalian species, provided sufficient amounts of fresh bone from the species is available. The empirical development of the procedure, coupled with the availability of fresh calf bone, has enabled isolation of substantially pure bovine osteogenic protein (BOP). BOP has been characterized significantly as set forth below; its ability to induce cartilage and ultimately endochondral bone growth in cat, rabbit, and rat have been studied; it has been shown to be able to induce the full developmental cascade of bone osteogenesis previously ascribed to unknown protein or proteins in heterogeneous bone extracts; and it may be used to induce formation of endochondral bone in non-union fractures. In its native form it is a glycosylated, dimeric protein. It has been partially sequenced. Its primary structure includes the amino acid sequences:

(1) D-F-D-A-Y-Y-C-S-G-A-C-Q-F-P-S,
(2) S-L-P-S-N-Y-A-T-I-Q-S-I-V
(3) T-C-C-V-P-E-L-S-A-I-S-M-L-Y-L-D-E-N
(4) M-S-S-L-B-I-L-F-F-D-E-N
(5) S-Q-E-L-Y-V-D-F--R
(6) F-L-H-C-Q-F-S-E-R-N-S
(7) T-V-G-Q-L-N-E-Q-S-S-E-P-N-I-Y
(8) I-Y-D-P-M-V-V

Elucidation of the amino acid sequence of BOP enables the construction of pools of nucleic acid probes encoding peptide fragments. Also, a concensus nucleic acid sequence designed as disclosed herein based on the amino acid sequence data, inferred codons for the sequences, and observation of partial homology with known genes may also be used as a probe. The probes may be used to isolate naturally occuring mRNAs and DNAs which encode active mammalian osteogenic proteins (OP) as described below using standard hybridization methodology. The mRNAs are present in the cytoplasm of cells of various species which are known to synthesize osteogenic proteins. Useful cells harboring the mRNAs include, for example, osteoblasts from bone or osteosarcoma, hypertrophic chondrocytes, and stem cells. The mRNAs can be converted into cDNA libraries. Relevant DNAs encoding osteogenic protein also are present in cloned genomic DNA libraries from various mammalian species.

When sequencing of the protein is complete, synthetic DNAs encoding the natural material, truncated forms, muteins, analogs, fusion proteins, and various other allelic variants and constructs can be synthesized using well known techniques and automated, commercially available equipment. These can be expressed using equally well established recombinant DNA technologies in prokaryotic or eucaryotic host cells, and can be glycosylated and/or oxidized if necessary for activity in vitro.

The isolation procedure for obtaining the protein from bone, the nature of the matrix and other material aspects concerning the nature, utility, how to make, and how to use the subject matter claimed will be further understood from the following, which constitutes the best method currently known for practicing the invention.

I. PURIFICATION OF BOP

1. Preparation of Demineralized Bone

Demineralized bovine bone matrix is prepared by previously published procedures (Sampath and Reddi (1983) Proc. Natl. Acad. Sci. USA 80:6591–6595). Bovine diaphyseal bones (age 1–10 days) are obtained from a local slaughterhouse and used fresh. The bones are stripped of muscle and fat, cleaned of periosteum, demarrowed by pressure with cold water, dipped in cold absolute ethanol, and stored at −20° C. They are then dried and fragmented by crushing and pulverized in a large mill. Care is taken to prevent heating by using liquid nitrogen. The pulverized bone is milled to a particle size between 70–420 μm and is defatted by two washes of approximately two hours duration with three volumes of chloroform and methanol (3:1). The particulate bone is then washed with one volume of absolute ethanol and dried over one volume of anhydrous ether. The defatted bone powder is then demineralized with 20 volumes of 0.5N HCl at 4° C. for 24 hours. The acid is removed every eight hours and fresh acid is added. Finally, the demineralized bone powder is washed with a large volume of water until the wash solution has a neutral pH. The water may be removed by freeze-drying.

2. Dissociative Extraction and Ethanol Precipitation

Demineralized bone matrix thus prepared is dissociatively extracted with 20 volumes of 4M guanidine-HCl, 50 mM Tris-HCl, pH 7.0, containing protease inhibitors (5 mM benzamidine, 0.1M 6-aminohexanoic acid, 5 mM N-ethylmaleimide, 0.5 mM phenylmethylsulfonyfluoride) for 16 hr. at 4° C. The suspension is filtered through cheese cloth and centrifuged at 20,000×g for 15 min. at 4° C. The supernatant is collected and concentrated to one volume using an Amicon ultrafiltration YM-10 hollow fiber membrane. The concentrate is centrifuged (40,000×g for 30 min. at 40° C.), and the supernatant is then subjected to ethanol precipitation. To one volume of concentrate is added seven volumes of cold (−20° C.) absolute ethanol (100%), which is then kept at −20° C. for 30 min. The precipitate is obtained upon centrifugation at 10,000×g for 10 min. at 4° C. The resulting pellet is resuspended in 250 ml of 85% cold ethanol and recentrifuged. The precipitate is then lyophilized.

3. Heparin-Sepharose Chromatography-I

The ethanol precipitated, lyophilized, extracted crude protein is dissolved in 20 volumes of 6M urea, 50 mM Tris-HCl, pH 7.0 (Buffer A) containing 0.15M NaCl, and clarified by centrifugation at 20,000×g for 30 min. The supernatant is stirred for 15 min. with 50 volumes of hydrated heparin-sepharose (Pharmacia) equilibrated with Buffer A containing 0.15M NaCl. The heparin-Sepharose is pre-treated with Buffer A containing 1.0M NaCl prior to equilibration. The unadsorbed protein is collected by packing the resin into a column. After washing with three column volumes of initial buffer (Buffer A containing 0.15M NaCl), protein is eluted with Buffer A containing 0.5M NaCl. The absorption of the eluate is monitored continuously at 280 nm. The pool of protein eluted by 0.5M NaCl (approximately 20 column volumes) is collected and stored at −200° C.

Figure 2A:
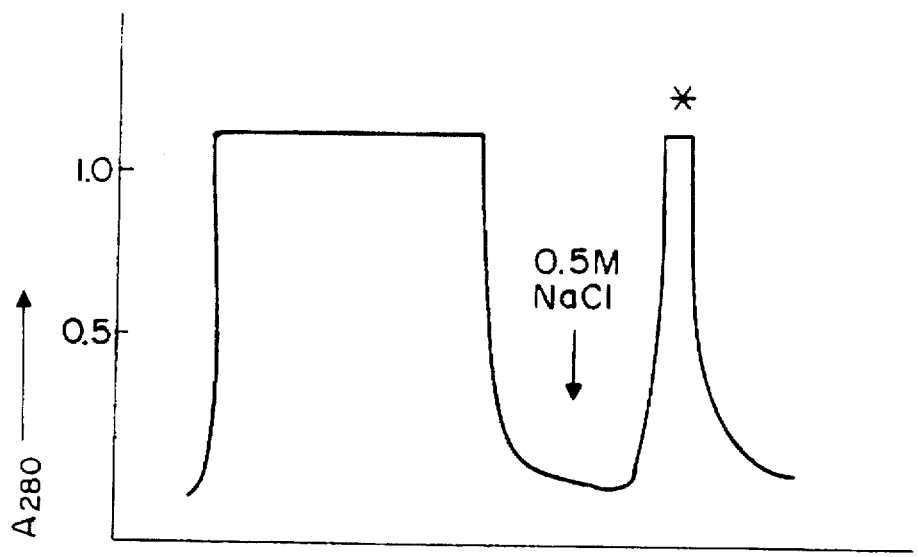
FIGS. 2A through 2D are a collection of plots of protein concentration (as indicated by optical absorption) vs elution volume illustrating the results of BOP fractionation during purification on (A) heparin-Sepharose-I; (B) HAP-Ultragel; (C) TSK 3000; and (D) heparin-Sepharose-II. *indicates biological activity.

As shown in FIG. 2A, most of the protein (about 95%) remains unbound. Approximately 5% of the protein is bound to the column. The unbound fraction has no bone inductive activity when bioassayed as a whole or after a partial purification through Sepharose CL-6B.

4. Hydroxyapaptite-Ultrogel Chromatography

Figure 2B:
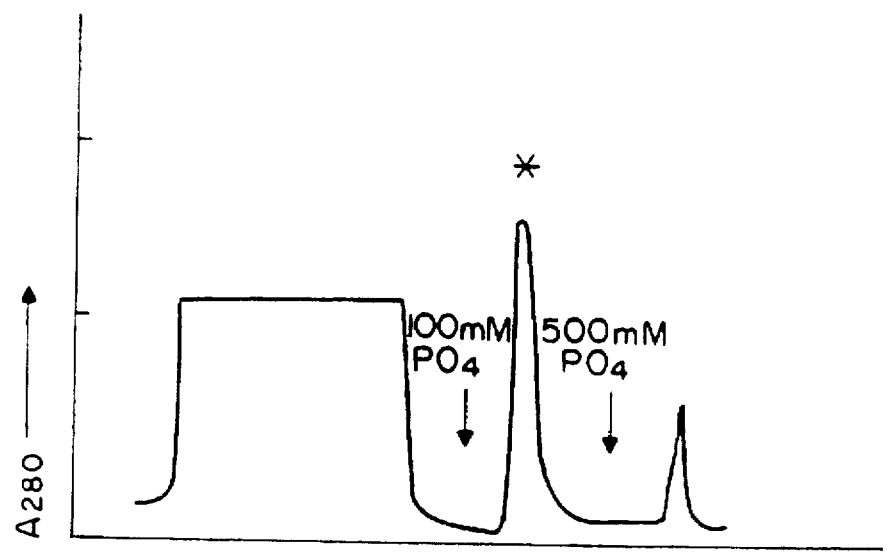

The volume of protein eluted by Buffer A containing 0.5M NaCl from the heparin-Sepharose is applied directly to a column of hydroxyapaptite-ultrogel (HAP-ultrogel) (LKB Instruments), and equilibrated with Buffer A containing 0.5M NaCl. The HAP-ultrogel is treated with Buffer A containing 500 mM Na phosphate prior to equilibration. The unadsorbed protein is collected as an unbound fraction, and the column is washed with three column volumes of Buffer A containing 0.5M NaCl. The column is subsequently eluted with Buffer A containing 100 mM Na Phosphate (see FIG. 2B). The approximately 3 column volume pool of the protein peak eluted by 100 mM Na phosphate is concentrated using an Amicon ultrafiltration YM-10 membrane to one volume, dialysed in a 3.5 kD molecular weight cut-off bag (Spectrapor) against distilled water, and lyophilized.

The eluted component can induce endochondral bone as measured by alkaline phosphatase activity and histology. As the biologically active protein is bound to HAP in the presence of 6M urea and 0.5M NaCl, it is likely that the protein has an affinity for bone mineral and may be displaced only by phosphate ions.

5. TSK 3000 Gel Exclusion Chromatography

Figure 2C:
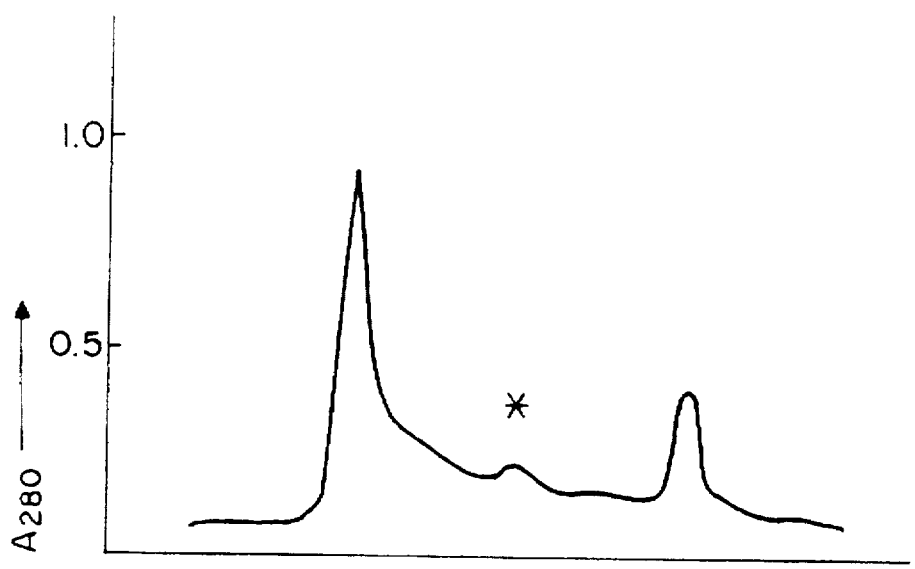

Analytical TSK 3000 gel (silica gel) is obtained from Bio Rad and equilibrated with 4M guanidine-HCl, 50 mm Tris-HCl, pH 7.0. A pre-column (analytical) is also used. A portion of the lyophilized protein from HA-ultrogel is dissolved in a known volume of 4M guanidine-HCl, 50 mM Tris-HCl, pH 7.0, and the solution is clarified by low speed centrifugation. A 200 μl sample containing approximately 10 mg of protein is loaded onto the column and then eluted with 4M guanidine-HCl, 50 mM Tris-HCl, pH 7.0, with a flow rate of 0.3 ml/min. 0.6 ml fractions are collected over 100 min., and the concentration of the protein is measured continuously at $A_{280}$. Fractions are collected and bioassayed as described below; fractions having a molecular weight less than 35 kD (30–34 kD) and osteoinductivity are pooled and stored at 4° C. (see FIG. 2C).

6. Heparin-Sepharose Chromatography-II

Figure 2D:
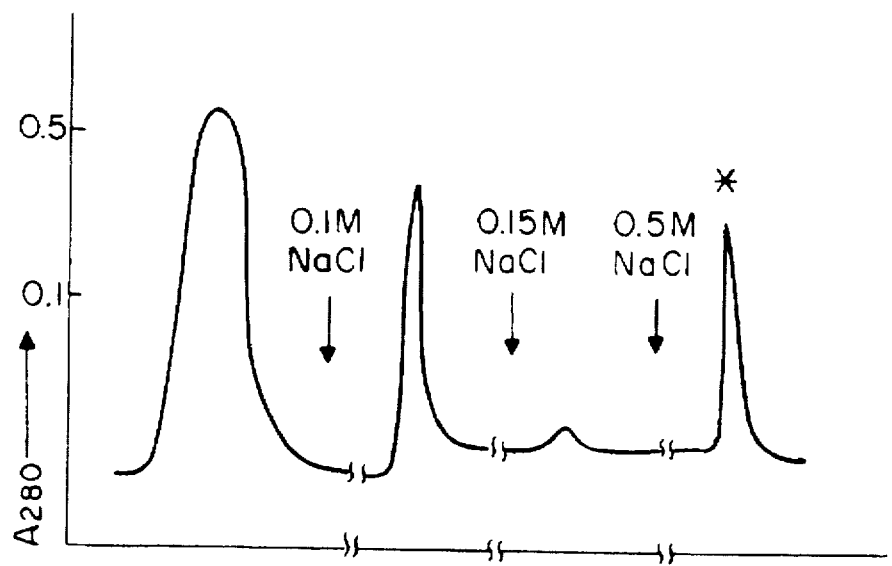

The pooled osteo-inductive fractions obtained from TSK gel exclusion chromatography are dialysed extensively against distilled water and then against one liter of 6M urea, 50 mM Tris-HCl, pH 7.0 (Buffer B). The dialysate is then cleared through centrifugation, and the supernatant is stirred for one hr. with 50–100 ml of hydrated heparin-sepharose (Pharmacia) equilibrated with Buffer B. The heparin-sepharose is pre-treated with Buffer B containing 1.0M NaCl prior to equilibration. The unadsorbed protein is collected by packing the resin into a column as an unbound fraction. After washing with three column volumes of initial buffer, the column is developed sequentially with Buffer B containing 0.1M NaCl, 0.15M NaCl, and 0.5M NaCl (see FIG. 2D). The protein eluted by 0.5M NaCl is collected and dialyzed extensively against distilled water. It is then dialyzed against one liter of 0.1% trifluoroacetic acid at 40° C.

7. Reverse Phase HPLC

Figure 8:
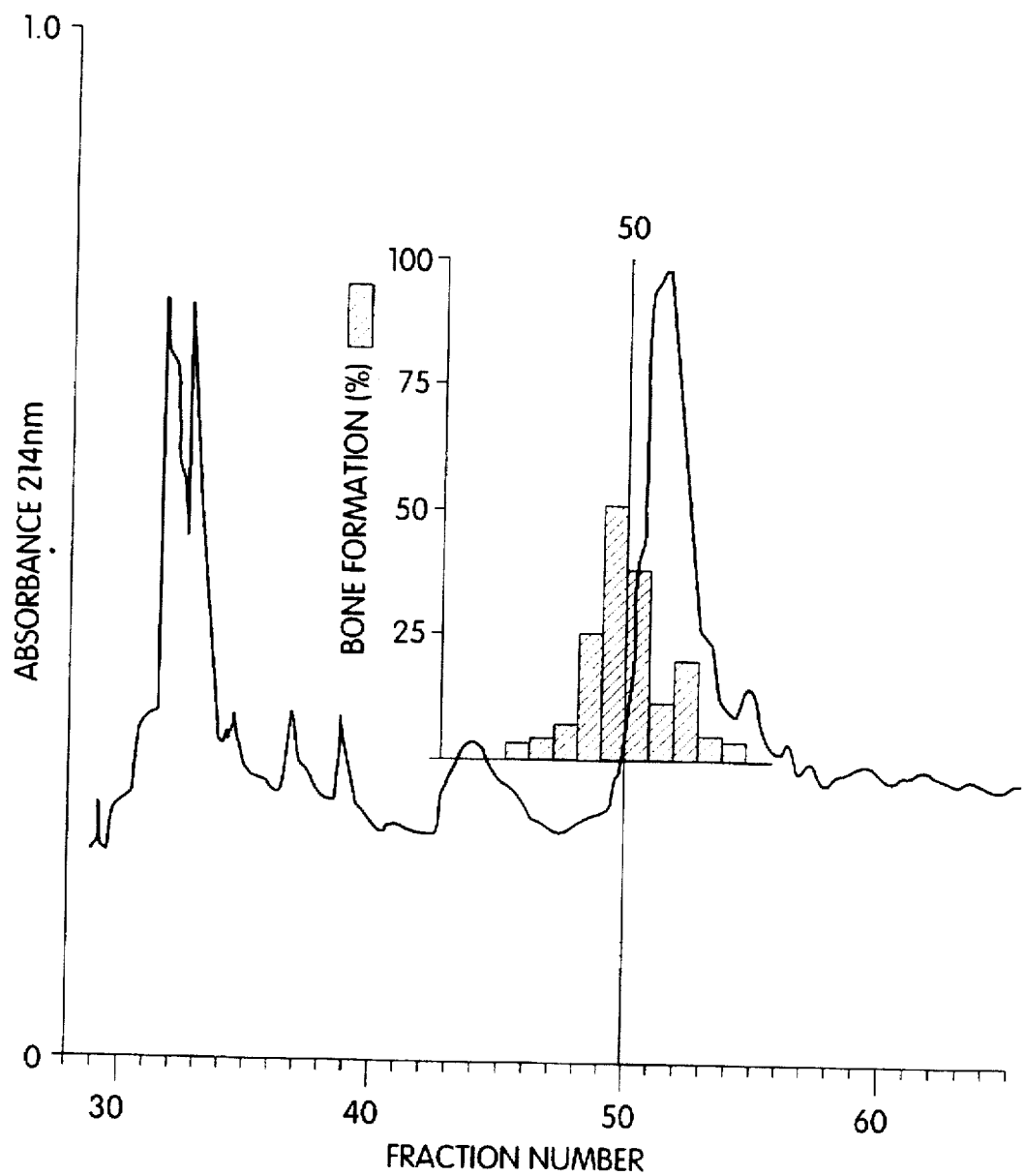
FIG. 8 is an HPLC chromatogram of an elution profile on reverse phase C-18 HPLC of the samples recovered from the second heparin-Sepharose chromatography step (see FIG. 2D). Superimposed is the percent bone formation in each fraction.

The final step before gel elution in the purification procedure is C-18 Vydac silica-based HPLC column chromatography (particle size 5 μm; pore size 300 Å). The osteoinductive fraction obtained from heparin-sepharose-II chromatograph is concentrated, loaded onto the column, and washed in 0.1% TFA, 10% acetonitrile for five min. As shown in FIG. 4, the bound proteins are eluted with a linear gradient of 10–30% acetonitrile over 15 min., 30–50% acetonitrile over 60 min, and 50–70% acetonitrile over 15 min at 22° C. with a flow rate of 1.0 ml/min. 1.0 ml/min, and 1.0 ml samples are collected in polycarbonate tubes. Protein is monitored by absorbance at 214 nm (FIG. 8). Column fractions are tested for the presence of concanavalin A-blottable 30 kD protein and then pooled. Pools are then characterized biochemically for the presence of 30 kD protein by autoradiography, concanavalin A blotting, and Coomassie blue dye staining. They are then assayed for in vivo osteogenic activity. Biological activity is not found in the absence of 30 kD protein.

8. Gel Elution

The final step in the purification of the 30 kD protein is elution from SDS gels. $^{125}$I-labelled 30 kD protein is routinely added to each preparation to monitor yields. Table 1 shows the various elution buffers that have been tested and the yields of $^{125}$I-labelled protein.

TABLE 1

Elution of 30 kD Protein from SDS Gel

| Buffer | 0.5 mm SDS Gel % Eluted |
| --- | --- |
| (1) dH$_2$O | 22 |
| (2) Guanidine-HCl, Tris-HCl, pH 7.0 | 2 |
| (3) Guanidine-HCl, 0.5% Triton, Tris-HCl, pH 7 | 93 |
|  | 52* |
| (4) 0.1% SDS, Tris-HCl, pH 7.0 | 98 |

*1.5 mm gel

Table 2 lists the steps used to isolate the 30 kD gel-bound proteins The standard protocol uses diffusion elution in Tris-HCl buffer containing 0.1% SDS to achieve greater than 95% elution of the protein from the 30 kD region of the gel.

TABLE 2

Preparation of Gel Eluted 30 kD Protein
(C-18 Pool plus $^{125}$I-labelled 30 kD protein)

1. Dry using vacuum centrifugation;
2. Wash pellet with H$_2$O;
3. Dissolve pellet in gel sample buffer (no reducing agent);
4. Electrophorese on pre-electrophoresed 0.5 mm mini gel;
5. Cut out 30 kD protein;
6. Elute from gel with 0.1% SDS, 50 mM Tris-HCl, pH 7.0;
7. Filter through Centrex membrane;
8. Concentrate in Centricon tube (10 kD membrane);
9. Chromatograph of TSK-3000 gel filtration column;
10. Concentrate in Centricon tube.

Chromatography in 0.1% SDS on a TSK-3000 gel filtration column is performed to separate gel impurities, such as soluble acrylamide, from the final product. The overall yield of labelled 30 kD protein from the gel elution protocol is 50–60% of the loaded sample. Most of the loss occurs in the electrophoresis step, due to protein aggregation and/or smearing. In a separate experiment, a sample of gel eluted 30 kD protein is reduced, electrophoresed on an SDS gel, and transferred to an Immobilon membrane. The membrane is stained with Coomassie blue dye, cut into slices, and the slices are counted. Coomassie blue dye stains the 16 kD and 18 kD reduced species almost exclusively. However, the counts showed significant smearing throughout the gel in addition to being concentrated in the 16 kD and 18 kD species. This suggests that the $^{125}$I-label can exhibit anomolous behavior on SDS gels and cannot be used as an accurate marker for cold protein under such circumstances.

The yield is 0.5 to 1.0 μg substantially pure osteogenic protein per kg of mineralized bone.

II. CHARACTERIZATION OF BOP

1. Molecular Weight and Structure

Electrophoresis of these fractions on nonreducing SDS polyacrylamide gels reveals a single band at about 30 kD as detected by both Coomassie blue staining (see FIG. 3A) and autoradiography.

In order to extend the analysis of BOP, the protein was examined under reducing conditions. FIG. 3B shows an SDS gel of BOP in the presence of dithiothreitol. Upon reduction, 30 kD BOP yields two species which are stained with Coomassic blue dye: a 16 kD species and an 18 kD species. Reduction causes loss of biological activity. Methods for the efficient elution of the proteins from SDS gels have been tested, and a protocol has been developed to achieve purification of both proteins. The two reduced BOP species have been analyzed to determine if they are structurally related. Comparison of the amino acid composition of the two proteins (as disclosed below) shows little differences, indicating that the native protein may comprise two chains having some homology.

2. Charge Determination

Isoelectric focusing studies are initiated to further evaluate the 30 kD protein for possible heterogeneity. Results to date have not revealed any such heterogeneity. The oxidized and reduced species migrate as diffuse bands in the basic region of the isoelectric focusing gel, using the iodinated 30 kD protein for detection. Using two dimensional gel electrophoresis and con A for detection, the oxidized 30 kD protein show one species migrating in the same basic region as the iodinated 30K protein. The diffuse character of the band may be traced to the presence of carbohydrate attached to the protein.

3. Presence of Carbohydrate

The 30 kD protein has been tested for the presence of carbohydrate by concanavalin A (con A) blotting after SDS-PAGE and transfer to nitrocellulose paper. The results demonstrate that the 30 kD protein has a high affinity for con A, indicating that the protein is glycosylated (FIG. 4A). In addition, the con A blots provide evidence for a substructure in the 30 kD region of the gel, suggesting heterogeneity due to varying degrees of glycosylation. After reduction (FIG. 4B), con A blots show evidence for two major components at 16 kD and 18 kD. In addition, it has been demonstrated that no glycosylated material remains at the 30 kD region after reduction.

In order to confirm the presence of carbohydrate and to estimate the amount of carbohydrate attached, the 30 kD protein is treated, with N-glycanase, a deglycosylating enzyme with a broad specificity. Samples of the $^{125}$I-labelled 30 kD protein are incubated with the enzyme in the presence of SDS for 24 hours at 37° C. As observed by SDS-PAGE, the treated samples appear as a prominent species at about 27 kD (FIG. 5A). Upon reduction, the 27 kD species is reduced to species having a molecular weight of about 14 kD–16 kD (FIG. 5B).

4. Chemical and Enzymatic Cleavage

Pilot cleavage reactions with CNBr are analyzed using con A binding for detection of fragments associated with carbohydrate. Cleavage reactions are conducted using trifluoroacetic acid (TFA) in the presence and absence of CNBr. Reactions are conducted at 37° C. for 18 hours, and the samples are vacuum dried. The samples are washed with water, dissolved in SDS gel sample buffer with reducing agent, boiled and applied to an SDS gel. After electrophoresis, the protein is transferred to Immobilon membrane and visualized by con A binding. In low concentrations of acid (1%), CNBr cleaves the majority of 16 kD and 18 kD species to one product, a species about 14 kD. In reactions using 10% TFA, a 14 kD species is observed both with and without CNBr.

Figure 6:
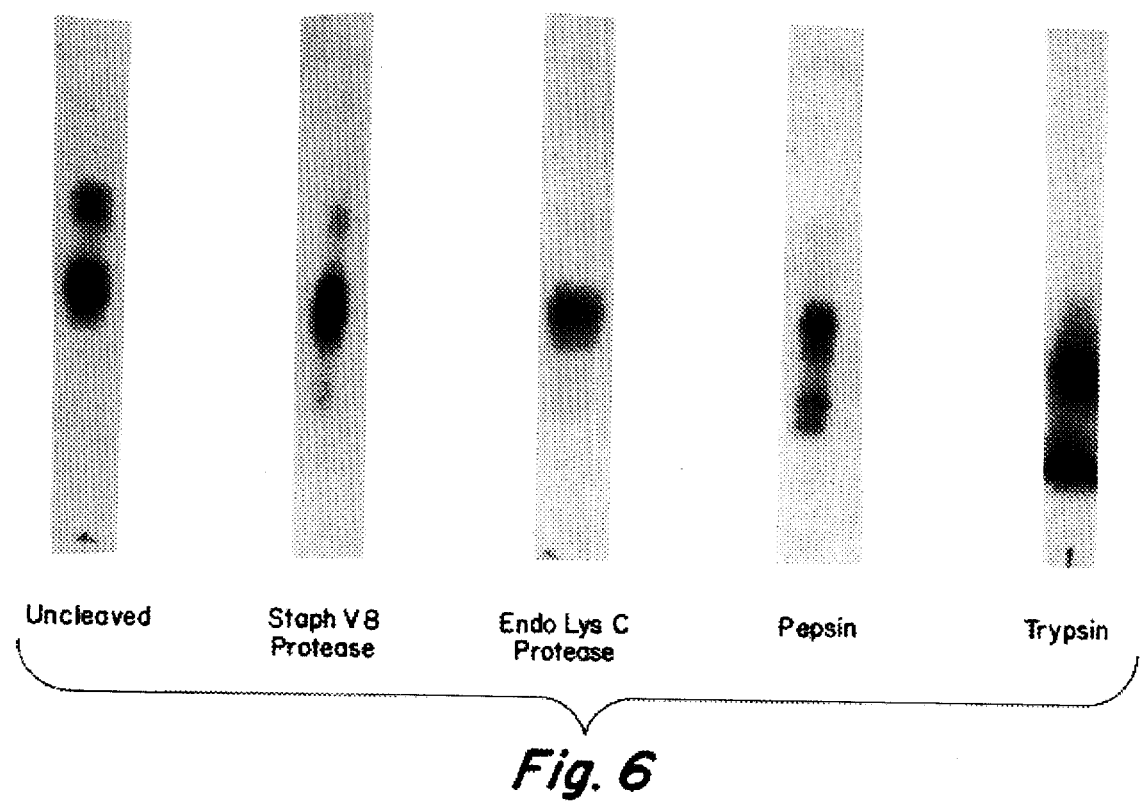
FIG. 6 is a photographic reproduction of an autoradiogram of an SDS polyacrylamide gel of peptides produced upon the digestion of the 30 kD osteogenic protein with V-8 protease, pepsin, trypsin, and Endo Lys C protease.

Four proteolytic enzymes are used in pilot experiments to examine the digestion products of the 30 kD protein: 1) V-8 protease; 2) Endo Lys C protease; 3) pepsin; and 4) trypsin. Except for pepsin, the digestion buffer for the enzymes is 0.1M ammonium bicarbonate, pH 8.3. The pepsin reactions are done in 0.1% TFA. The digestion volume is 100 μl and the ratio of enzyme to substrate is 1:10. $^{125}$I-labelled 30 kD OP is added for detection. After incubation at 37° C. for 16 hr., digestion mixtures are dried down and taken up in gel sample buffer containing dithiothreitol for SDS-PAGE. FIG. 6 shows an autoradiograph of an SDS gel of the digestion products. The results show that under these conditions, only trypsin digests the reduced 16 kD/18 kD species completely and yields a major species at around 12 kD. Pepsin digestion yields better defined, lower molecular weight species. However, the 16 kD/18 kD fragments were not digested completely. The V-8 digest shows limited digestion with one dominant species at 16 kD.

5. Sequencing

Figure 7:
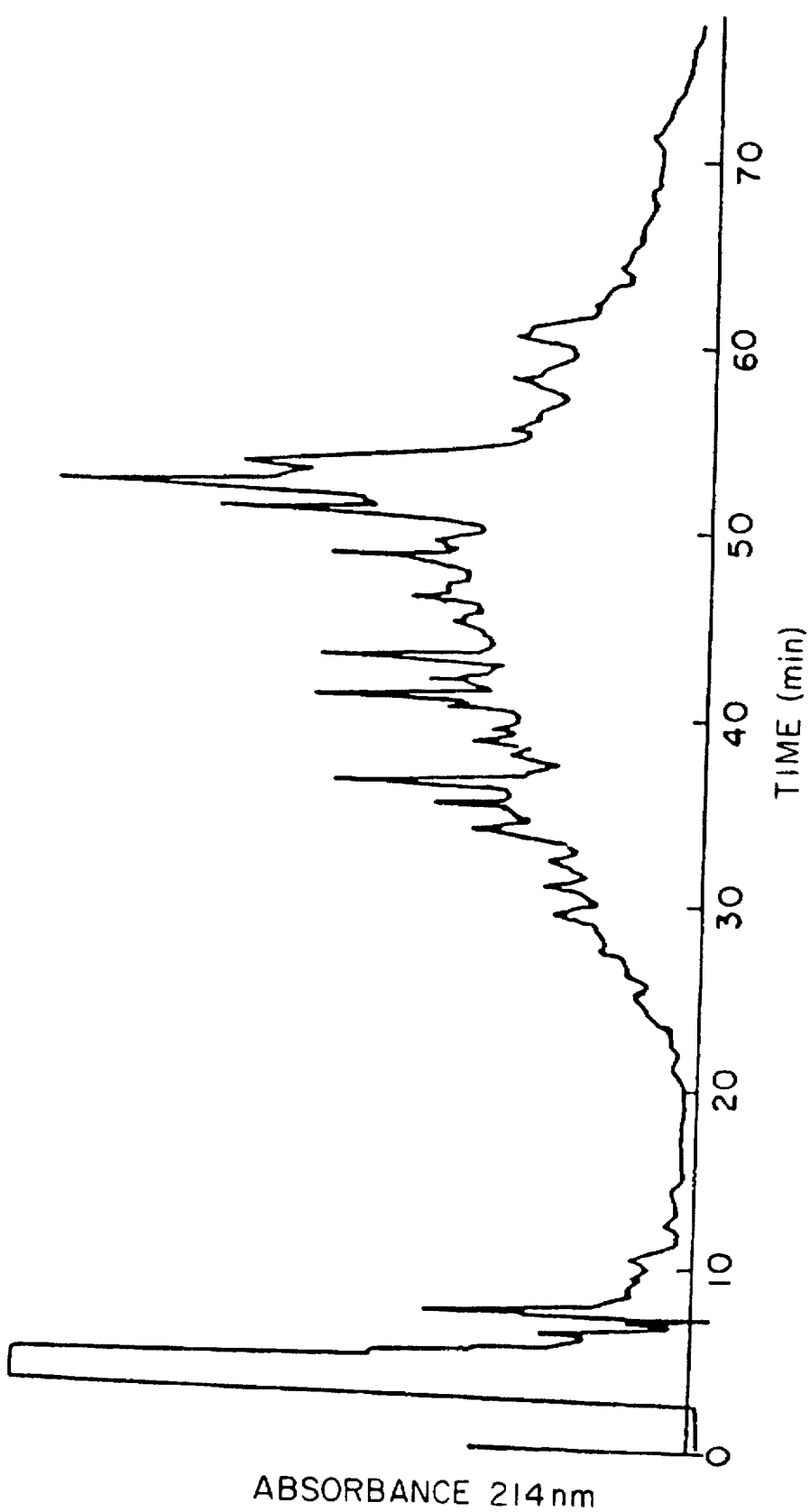
FIG. 7 is an HPLC chromatogram of tryptic peptides of BOP.

To obtain amino acid sequence data, the protein is cleaved with trypsin. The tryptic digest of reduced and carboxymethylated 30 kD protein (approximately 13 μg) is fractionated by reverse-phase HPLC using a C-8 narrowbore column (13 cm×2.1 mm ID) with a TFA/acetonitrile gradient and a flow rate of 150 μl/min. The gradient employs (A) 0.06% TFA in water and (B) 0.04% TFA in water and acetonitrile (1:4; v:v). The procedure was 10% B for five min., followed by a linear gradient for 70 min. to 80% B, followed by a linear gradient for 10 min. to 100% B. Fractions containing fragments as determined from the peaks in the HPLC profile (FIG. 7) are rechromatographed at least once under the same conditions in order to isolate single components satisfactory for sequence analysis.

Various of the peptide fragments produced using the foregoing procedures have been analyzed in an automated amino acid sequencer (Applied Biosystems 450A). To date, the following sequence data has been obtained:

(1) D-F-D-A-Y-Y-C-S-G-A-C-Q-F-P-S (2) S-L-K-P-S-N-Y-A-T-I-Q-S-I-V (3) T-C-C-V-P-E-L-S-A-I-S-M-L-Y-L-D-E-N (4) M-S-S-L-S-I-L-F-F-D-E-N (5) S-Q-E-L-Y-V-D-F-Q-R (6) F-L-H-C-Q-F-S-E-R-N-S (7) T-V-G-Q-L-N-E-Q-S-S-E-P-N-I-Y (8) I-Y-D-P-M-V-V.

6. Amino Acid Analysis

Strategies for obtaining amino acid composition were developed using gel elution from 15% SDS gels, transfer onto Immobilon, and hydrolysis. Immobilon membrane is a polymer of vinylidene difluoride and, therefore, is not susceptible to acid cleavage. Samples of oxidized (30 kD) and reduced (16 kD and 18 kD) BOP are electrophoresed on a gel and transferred to Immobilon for hydrolysis and analysis as described below. The composition data generated by amino acid analyses of 30 kD BOP is reproducible, with some variation in the number of residues for a few amino acids, especially cysteine, and isoleucine.

Samples are run on 15% SDS gels, transferred to Immobilon, and stained with Coomassie blue. The bands of interest are excised from the Immobilon, with a razor blade and placed in a Corning 6×50 test tube cleaned by pyrolysis at 550° C. When cysteine is to be determined, the samples are treated with performic acid, which converts cysteine to cysteic acid. Cysteic acid is stable during hydrolysis with HCl, and can be detected during the HPLC analysis by using a modification of the normal Pico Tag eluents (Millipore) and gradient. The performic acid is made by mixing 50 μl 30% hydrogen peroxide with 950 μl 99% formic acid, and allowing this solution to stand at room temperature for 2 hr. The samples are then treated with performic acid (PFA); 20 μl PFA is pippetted onto each sample and placed in an ice bath at 4° C. for 2.5 hours. After 2.5 hr. the PFA is removed by drying in vacuo, and the samples are then hydrolyzed. A standard protein of known composition and concentration containing cysteine is treated with PFA and hydrolyzed concurrently with the OP samples.

The hydrolysis of the OP samples is done in vacuo. The samples, with empty tubes and Immobilon blanks, are placed in a hydrolysis vessel which is placed in a dry ice/ethanol bath to keep the HCl from prematurely evaporating. 200 μl 6N HCl containing 2% phenol and 0.1% stannous chloride are added to the hydrolysis vessel outside the tubes containing the samples. The hydrolysis vessel is then sealed, flushed with prepurified nitrogen, evacuated, and then held at 115° C. for 24 hours, after which time the HCl is removed by drying in vacuo.

After hydrolysis, each piece of Immobilon is transferred to a fresh tube, where it is rinsed twice with 100 μl 0.1% TFA, 50% acetonitrile. The washings are returned to the original sample tube, which is then redried as below. A similar treatment of amino acid analysis on Immobilon can be found in the literature (LeGendre and Matsudaira (1988) Biotechniques 6:154–159).

The samples are redried twice using 2:2:1ethanol:water:triethylamine and allowed to dry at least 30 min. after each addition of redry reagent. These redrying steps bring the sample to the proper pH for derivatization.

The samples are derivatized using standard methodology. The solution is added to each sample tube. The tubes are placed in a desiccator which is partially evacuated, and are allowed to stand for 20min. The desiccator is then fully evacuated, and the samples are dried for at least 3 hr. After this step the samples may be stored under vacuum at −20° C. or immediately diluted for HPLC. The samples are diluted with Pico Tag Sample Diluent (generally 100 μl) and allowed to stand for 20 min., after which they are analyzed on HPLC using the Pico Tag chromatographic system with some minor changes involving gradients, eluents, initial buffer conditions and oven temperature.

After HPLC analysis, the compositions are calculated. The molecular weights are assumed to be 14.4 kD, 16.2 kD, and 27 kD. The number of residues is approximated by dividing the molecular weight by the average molecular weight per amino acid, which is 115. The total picomoles of amino acid recovered is divided by the number of residues, and then the picomoles recovered for each amino acid is divided by the number of picomoles per residue, determined above. This gives an approximate theoretical number of residues of each amino acid in the protein. Glycine content may be overestimated in this type of analysis.

Composition data obtained are shown in TABLE 4.

TABLE 4

| AMINO ACID | BOP Amino Acid Analyses | | |
|---|---|---|---|
| | 30 kD[3] | 16 kD[3] | 18 kD[3] |
| Aspartic Acid/Asparagine | 22 | 11 | 13 |
| Glutamic Acid/Glutamine | 24 | 12 | 15 |
| Serine[2] | 24 | 14 | 20 |
| Glycine[2] | 29 | 19 | 27 |
| Histidine* | 5 | * | * |
| Arginine | 13 | 6 | 6 |
| Threonine | 11 | 6 | 6 |
| Alanine | 18 | 10 | 10 |
| Proline | 14 | 6 | 5 |
| Tyrosine | 11 | 3 | 2 |
| Valine | 14 | 7 | 6 |
| Methionine | 3 | 0 | 1 |
| Cysteine[1] | 16 | 11 | 10 |
| Isoleucine | 15 | 13 | 9 |
| Leucine | 15 | 7 | 8 |
| Phenylalanine | 7 | 3 | 4 |
| Tryptophan | ND | ND | ND |
| Lysine | 12 | 5 | 6 |

*Histidine results are not integrated because histidine is present in low quantities.
[1]Cysteine is corrected by percent normally recovered from performic acid hydrolysis of the standard protein.
[2]Serine and Glycine levels are sometimes elevated in gel-eluted samples.
[3]These molecular weights reflect mobility on gels. The compositions calculated are based on the 30 kD protein including 10% by weight carbohydrate.

III. DEMONSTRATION THAT THE 30 KD PROTEIN IS OSTEOGENIC PROTEIN

1. Gel Slicing:

Gel slicing experiments confirm that the isolated 30 kD protein is the protein responsible for osteogenic activity.

Figure 14:
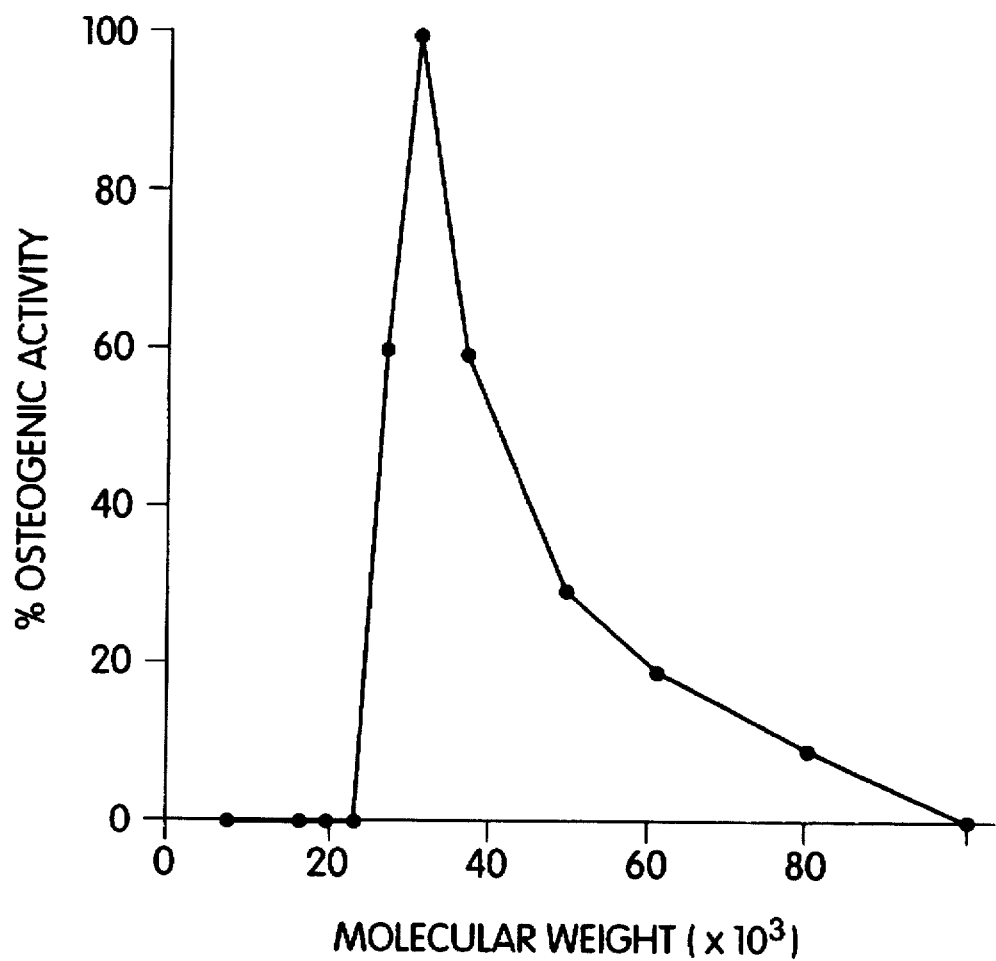
FIG. 14 is a graph of osteogenic activity vs. increasing molecular weight showing peak bone forming activity in the 30 kD region of an SDS polyacrylamide gel.

Gels from the last step of the purification are sliced. Protein in each fraction is extracted in buffer containing 4M guanidine-HCl, 0.5% non-ionic detergent (Triton X-100), 50 mM Tris-HCl, 0.1 SDS. The extracted proteins are desalted, concentrated, and assayed for endochondral bone formation activity. The results are set forth in FIG. 14. Activity in higher molecular weight regions is apparently due to protein aggregation. These protein aggregates, when reduced, yields the 16 kD and 18 kD species discussed above.

2. Con A-Sepharose Chromatography:

A sample containing the 30 kD protein is solubilized using 0.1% SDS, 50 mM Tris-HCl, and is applied to a column of con A-Sepharose equilibrated with the same buffer. The bound material is eluted in SDS Tris-HCl buffer containing 0.5M alpha-methyl mannoside. After reverse phase chromatography of both the bound and unbound fractions, con A-bound materials, when implanted, result in extensive bone formation. Further characterization of the bound materials show a con A-blottable 30 kD protein. It accordingly is the 30 kD glycosylated protein that is responsible for the bone forming activity.

Figure 9:
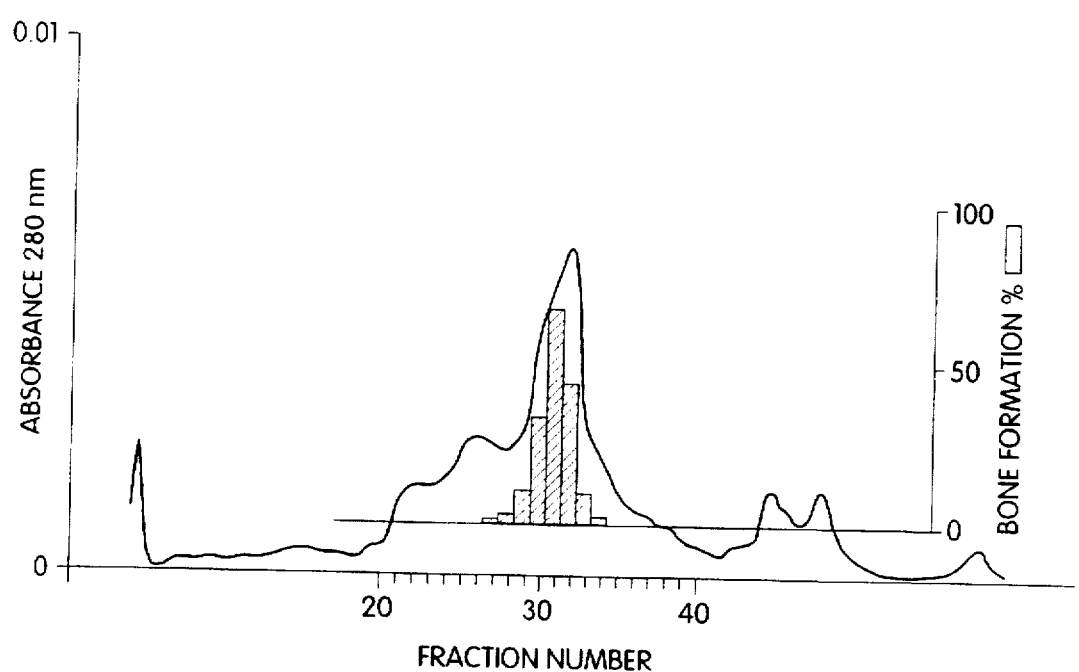
FIG. 9 is a gel permeation chromatogram of an elution profile on TSK 3000/2000 gel of the C-18 purified osteogenic peak fraction. Superimposed is the percent bone formation in each fraction.

3. Gel Permeation Chromatography:

TSK-3000/2000 gel permeation chromatography in guanidine-HCl is used to achieve separation of the high specific activity fraction obtained from C-18 chromatography (FIG. 9). The results demonstrate that the peak of bone inducing activity elutes in fractions containing substantially pure 30 kD protein by Coomassie blue staining. When this fraction is iodinated and subjected to autoradiography, a strong band at 30 kD accounts for 90% of the iodinated proteins. The fraction induces bone formation in vivo at a dose of 50 to 100 ng per implant.

4. Structural Requirements for Biological Activity

Although the role of 30 kD OP is clearly established for bone induction, through analysis of proteolytic cleavage products we have begun to search for a minimum structure that is necessary for activity in vivo. The results of cleavage experiments demonstrate that pepsin treatment fails to destroy bone inducing capacity, whereas trypsin or CNBr completely abolishes the activity.

An experiment is performed to isolate and identify pepsin digested product responsible for biological activity. Sample used for pepsin digest were 20%–30% pure. The buffer used is 0.1% TFA in water. The enzyme to substrate ratio is 1:10. A control sample is made without enzyme. The digestion mixture is incubated at room temperature for 16 hr. The digested product is then separated in 4M guanidine-HCl using gel permeation chromatography, and the fractions are prepared for in vivo assay. The results demonstrate that active fractions from gel permeation chromatography of the pepsin digest correspond to molecular weight of 8 kD–10 kD.

IV. PURIFICATION OF HUMAN OSTEOGENIC PROTEIN

Human bone is obtained from the Bone Bank, (Massachusetts General Hospital, Boston, Mass.), and is milled, defatted, demarrowed and demineralized by the procedure disclosed above. 320 g of mineralized bone matrix yields 70–80 g of demineralized bone matrix. Dissociative extraction and ethanol precipitation of the matrix gives 12.5 g of guanidine-HCl extract.

Figure 10A:
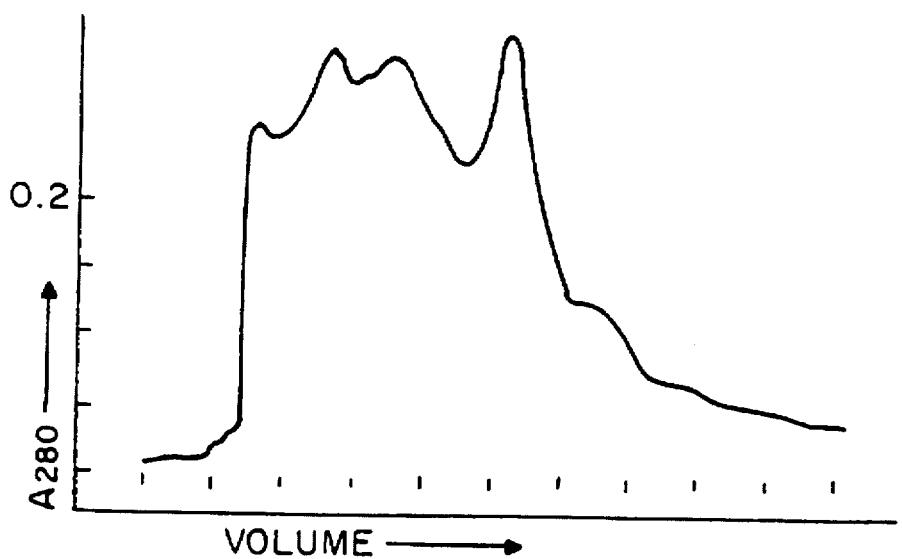
FIGS. 10A through 10D are a collection of graphs of protein concentration (as indicated by optical absorption) vs. elution volume illustrating the results of protein fractionation on (A) TSK 3000; (B) HAP-Ultragel; (C) heparin-Sepharose; and (D) reverse phase HPLC on C-18.
Figure 10B:
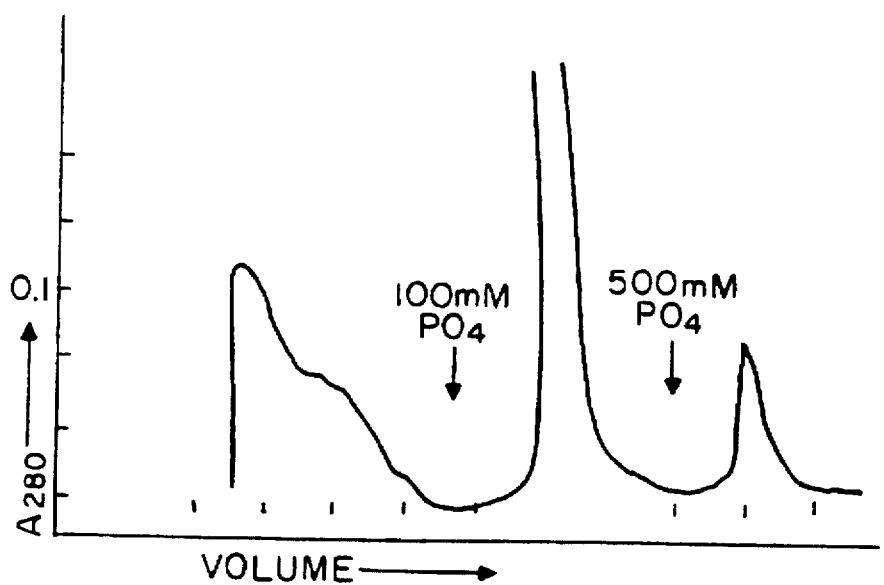
Figure 10C:
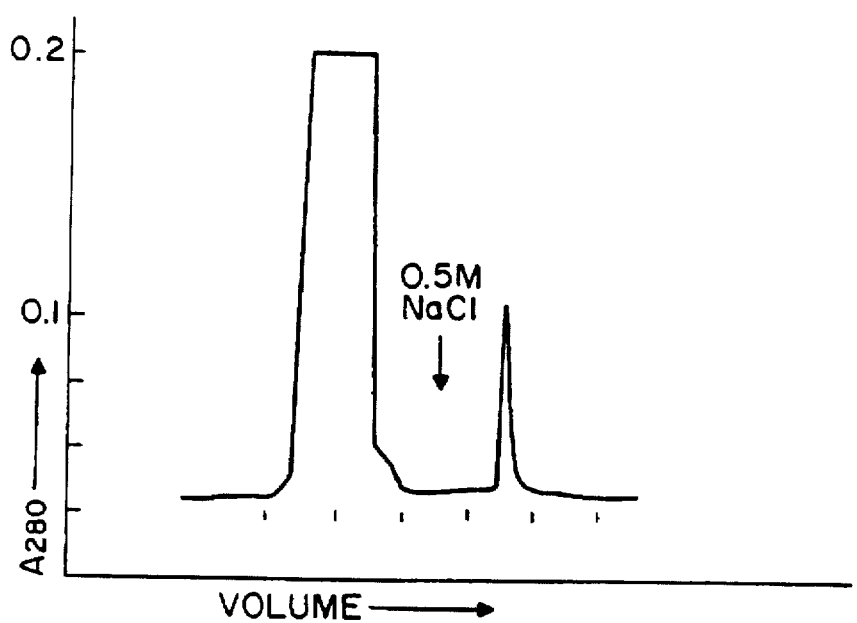
Figure 10D:
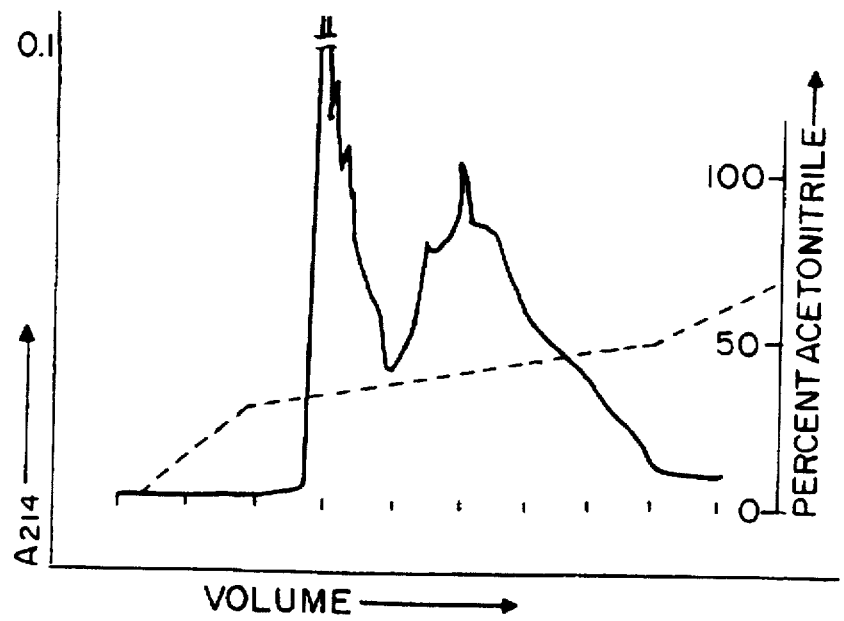

One third of the ethanol precipitate (0.5 g) is used for gel filtration through 4M guanidine-HCl (FIG. 10A). Approximately 70–80 g of ethanol precipitate per run is used. In vivo bone inducing activity is localized in the fractions containing proteins in the 30 kD range. They are pooled and equilibrated in 6M urea, 0.5M NaCl buffer, and applied directly onto a HAP column; the bound protein is eluted stepwise by using the same buffer containing 100 mM and 500 mM phosphate (FIG. 10B). Bioassay of HAP bound and unbound fractions demonstrates that only the fraction eluted by 100 mM phosphate has bone inducing activity in vivo. The biologically active fraction obtained from HAP chromatography is subjected to heparin-Sepharose affinity chromatography in buffer containing low salt; the bound proteins are eluted by 0.5M NaCl (FIG. 10C). Assaying the heparin-Sepharose fractions shows that the bound fraction eluted by 0.5M NaCl have bone-inducing activity. The active fraction is then subjected to C-18 reverse phase chromatography. (FIG. 10D).

The active fraction can then be subjected to SDS-PAGE as noted above to yield a band at about 30 kD comprising substantially pure human osteogenic protein.

IV. ANIMAL STUDIES

Substantially pure BOP and BOP-rich extracts comprising protein having the properties set forth above have been incorporated in matricies to produce osteogenic devices, tested in rat, cat, and rabbit models, and found to be potent inducers of osteogenesis, ultimately resulting in formation of mineralized, endochondral bone. Studies in rats show the osteogenic effect to be dependent on the dose of OP dispersed in the osteogenic device. No activity is observed if the protein is not first dispersed in a matrix. The following sets forth guidelines for how the osteogenic devices disclosed herein might be used in a clinical setting, a protocol for determining active fractions of OP when employing the isolation procedure of the invention, and details of the construction and nature of useful matricies.

1. Rat Model

A. Bioassay

The bioassay for bone induction as described by Sampath and Reddi (Proc. Natl. Acad. Sci. USA (1983) 80:6591–6595), herein incorporated by reference, is used to establish the efficacy of the purification protocols. This assay consists of implanting the test samples in subcutaneous sites in allogeneic recipient rats under ether anesthesia. A vertical incision (1 cm) is made under sterile conditions in the skin over the thoraic region, and a pocket is prepared by blunt dissection. Approximately 25 mg of the test sample is implanted deep into the pocket and the incision is closed with a metallic skin clip. The heterotopic site allows for the study of bone induction without the possible ambiguities resulting from the use of orthotopic sites.

B. Fabrication of Osteogenic Devices

Demineralized bone matrix is prepared from the dehydrated diaphyseal shafts of rat femur and tibia as described herein to produce a bone particle size which pass through a 420 µm sieve. The bone particles are subjected to dissociative extraction with 4M guanidine-HCl. Such treatment results in a complete loss of the inherent ability of the bone matrix to induce endochondral bone differentiation. The remaining insoluble material is used to fabricate the matrix. The material is mostly collagenous in nature, and upon implantation, does not induce cartilage and bone. All new preparations are tested for mineral content and false positives before use. The total loss of biological activity of bone matrix is restored when an active osteoinductive protein fraction or a pure protein is reconstituted with the biologically inactive insoluble collagenous matrix. The osteoinductive protein can be obtained from any vertabrates, e.g., bovine, porcine, monkey, or human, a produced using recombinant DNA techniques.

The carrier used herein may be replaced by either a biodegradable-synthetic or synthetic-inorganic matrix (e.g., HAP, collagen, tricalcium phosphate, or polylactic acid, polyglycolic acid and various copolymers thereof).

Studies have shown that surface charge, particle size, the presence of mineral, and the methodology for combining matrix and OP all play a role in achieving successful bone induction. Perturbation of the charge by chemical modification abolishes the inductive response. Particle size influences the quantitative response of new bone; particles between 75 and 420 µm elicit the maximum response. Contamination of the matrix with bone mineral will inhibit bone formation. Most importantly, the procedures used to formulate OP onto the matrix are extremely sensitive to the physical and chemical state of both the OP and the matrix.

The sequential cellular reactions in the interface of the bone matrix/OP implants are complex. The multistep cascade includes: binding of fibrin and fibronectin to implanted matrix, chemotaxis of cells, proliferation of fibroblasts, differentiation into chondroblasts, cartilage formation, vascular invasion, bone formation, remodeling, and bone marrow differentiation.

A successful carrier for OP must perform several important functions. It must bind OP and act as a slow release delivery system, accommodate each step of the cellular response during bone development, and protect the OP from nonspecific proteolysis. In addition, selected materials must be biocompatible in vivo and biodegradable; the carrier must act as a temporary scaffold until replaced completely by new bone. Polylactic acid (PLA), polyglycolic acid (PGA), and various combinations have different dissolution rates in vivo. In bones, the dissolution rates can vary according to whether the implant is placed in cortical or trabecular bone.

Matrix geometry, particle size, the presence of surface charge, and porosity or the presence of interstices among the particles of a size sufficient to permit cell infiltration, are all important to successful matrix performance. It is preferred to shape the matrix to the desired form of the new bone and to have dimensions which span non-union defects. Rat studies show that the new bone is formed essentially having the dimensions of the device implanted.

The matrix may comprise a shape-retaining solid made of loosely adhered particulate material, e.g., with collagen. It may also comprise a molded, porous solid, or simply an aggregation of close-packed particles held in place by surrounding tissue. Masticated muscle or other tissue may also be used. Large allogeneic bone implants can act as a carrier for the matrix if their marrow cavities are cleaned and packed with particles and the disposed OP.

To activate the matrix, a portion of the active protein (50 ng to 1,000 ng) dissolved in a known volume of 4M guanidine-HCl, is added to the inactive carrier matrix (e.g., 25 mg in rats). The mixture is vortexed many times at 4° C. Cold absolute ethanol (5 volumes) is added to the mixture, which is then kept at −20° C. for 30 min. After centrifugation (10,000×g for 10 min. at 4° C.), the supernatant is discarded. The reconstituted matrix is washed twice with 85% ethanol in water, lyophilized, and shaped as desired or implanted by packing.

C. Results

The implant model in rats exhibits a controlled progression through the stages of matrix induced endochondral bone development including: (1) transient infiltration by polymorphonuclear leukocytes on day one; (2) mesenchymal cell migration and proliferation on days two and three; (3) chondrocyte appearance on days five and six; (4) cartilage matrix formation on day seven; (5) cartilage calcification on day eight; (9) vascular invasion, appearance of osteoblasts, and formation of new bone on days nine and ten; (10) appearance of osteoblastic and bone remodeling and dissolution of the implanted matrix on days twelve to eighteen; and (11) hematopoietic bone marrow differentiation in the ossicle on day twenty-one. The results show that the shape of the new bone conforms to the shape of the implanted matrix.

Histological sectioning and staining is preferred to determine the extent of osteogenesis in the implants. Staining with toluidine blue or hemotoxylin/eosin demonstrates clearly the ultimate development of endochondrial bone. Twelve day implants are usually sufficient to determine whether the implants show bone inducing activity.

Alkaline phosphatase activity may be used as a marker for osteogenesis. The enzyme activity may be determined spectrophotometrically after homogenization of the implant. The activity peaks at 9–10 days in vivo and thereafter slowly declines. Implants showing no bone development by histology should have no alkaline phosphatase activity under these assay conditions. The assay is useful for quantitation and obtaining an estimate of bone formation very quickly after the implants are removed from the rat.

Implants containing osteogenic protein at several levels of purity have been tested to determine the most effective dose/purity level, in order to seek a formulation which could be produced on an industrial scale. The results as measured by alkaline phosphatase activity level, and histological evaluation and represented as "bone forming units". For example, one bone forming unit represents the amount of protein that is needed for half maximal bone forming activity of the implant on day 12.

Figure 11:
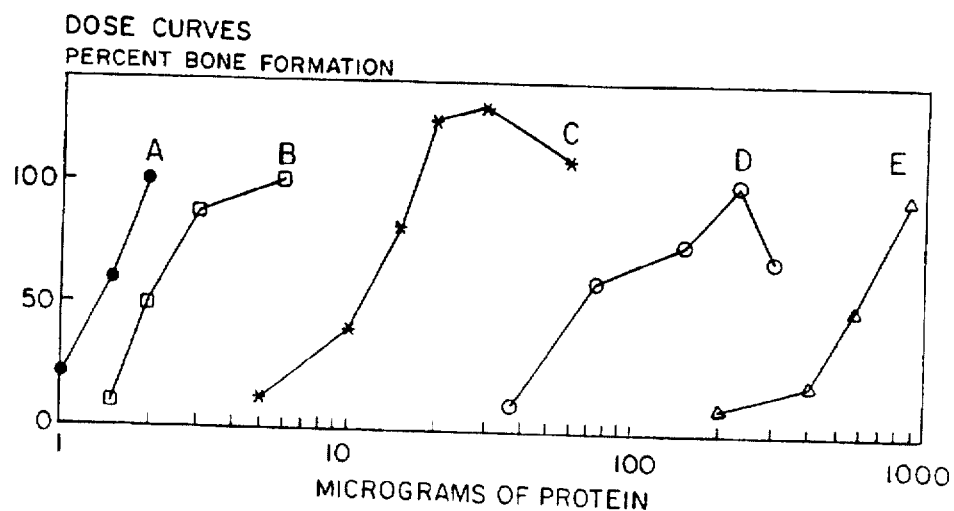
FIG. 11 is a graph showing representative dose curves for bone-inducing activity in samples of the various purification steps.

Dose curves are constructed for bone inducing activity in vivo at each step of the purification scheme by assaying various concentrations of protein. FIG. 11 shows representative dose curves. Approximately 10–12 µg of the TSK-fraction, 3–4 µg of heparin-Sepharose-II fraction, 0.5–1 µg of the C-18 column fraction, and 25–50 ng of gel eluted highly purified 30 kD protein is needed for unequivocal bone formation (half maximum activity).

2. Feline Model

The purpose of this study is to establish a large animal efficacy model for the testing of the osteogenic devices of the invention, and to characterize repair of massive bone defects and simulated fracture non-union encountered frequently in the practice of orthopedic surgery. The study is designed to evaluate whether implants of OP with a carrier can enhance the regeneration of bone following injury and major reconstructive surgery by use of this large mammal model. The first step in this study design consists of the surgical preparation of a femoral osteotomy defect which, without further intervention, would consistently progress to non-union of the simulated fracture defect. The effects of implants of osteogenic devices into the created bone defects were evaluated by the following study protocol.

A. Procedure

Sixteen adult cats weighing less than 10 lbs. undergo unilateral preparation of a 1 cm bone defect in the right femur through a lateral surgical approach. The femur is immediately internally fixed by lateral placement of an 8-hole plate to preserve the exact dimensions of the defect. There are three different types of materials implanted in the surgically created cat femoral defects: group I (n=3) is a control group which undergo the same plate fixation with implants of 4M guanidine-HCl-treated (inactivated) cat demineralized bone matrix powder (GuHCl-DBM) (360 mg); group II (n=3) is a positive control group implanted with biologically active demineralized bone matrix powder (DBM) (360 mg); and group III (n=10) undergo a procedure identical to groups I–II, with the addition of OP onto each of the GuHCl-DBM carrier samples. To summarize, the group III OP-treated animals are implanted with exactly the same material as the group II animals, but with the singular addition of osteogenic protein.

All animals are allowed to ambulate ad libitum within their cages post-operatively. All cats are injected with tetracycline (25 mg/kg SQ each week for four weeks) for bone labelling. All but four group III animals are sacrificed four months after femoral osteotomy.

B. Radiomorphometrics

Figure 12:
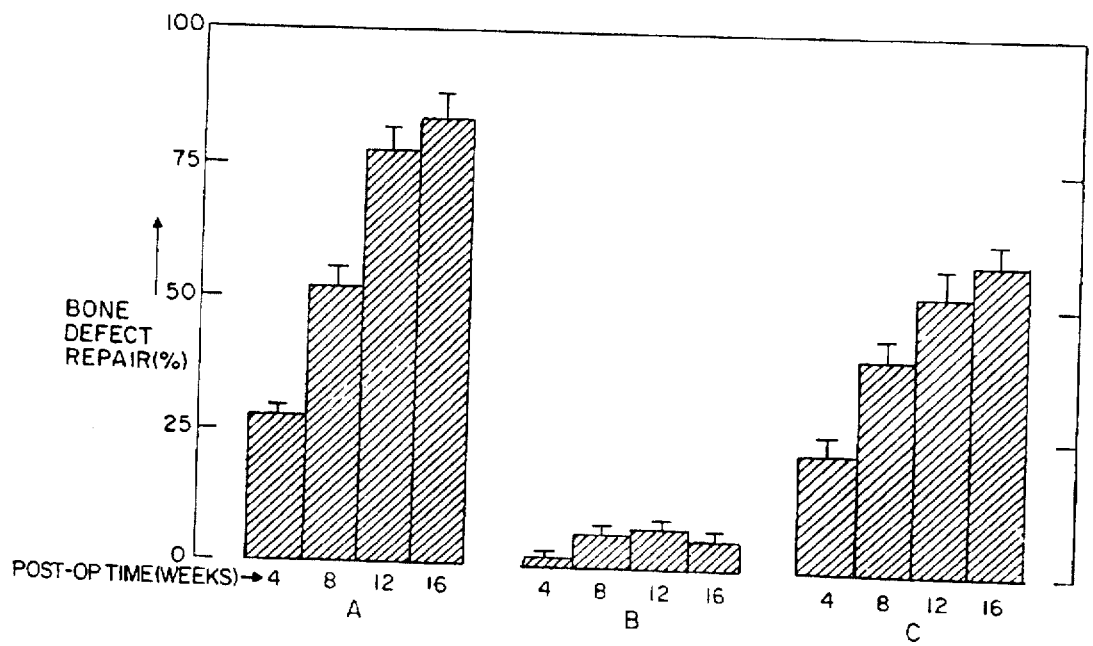
FIG. 12 is a bar graph of radiomorphometric analyses of feline bone defect repair after treatment with an osteogenic device (A), carrier control (B), and demineralized bone (C)

In vivo radiomorphometric studies are carried out immediately post-op at 4, 8, 12 and 16 weeks by taking a standardized x-ray of the lightly anesthesized animal positioned in a cushioned x-ray jig designed to consistently produce a true anterio-posterior view of the femur and the osteotomy site. All x-rays are taken in exactly the same fashion and in exactly the same position on each animal. Bone repair is calculated as a function of mineralization by means of random point analysis. A final specimen radiographic study of the excised bone is taken in two planes after sacrifice. X-ray results are shown in FIG. 12, and displaced as percent of bone defect repair. To summarize, at 16 weeks, 60% of the group III femors are united with average 86% bone defect regeneration. By contrast, the group I GuHCl-DMB negative-control implants exhibit no bone growth at four weeks, less than 10% at eight and 12 weeks, and 16% (±10%) at 16 weeks with one of the five exhibiting a small amount of bridging bone. The group II DMB positive-control implants exhibited 18% (±3%) repair at four weeks, 35% at eight weeks, 50% (±10%) at twelve weeks and 70% (±12%) by 16 weeks, a statistical difference of p<0.01 compared to OP at every month. One of the three (33%) is united at 16 weeks.

D. Biomechanics

Excised test and normal femurs are immediately studied by bone densitometry, wrapped in two layers of saline-soaked towels, placed in two sealed plastic bags, and stored at −20° C. until further study. Bone repair strength, load to failure, and work to failure are tested by loading to failure on a specially designed steel 4-point bending jig attached to an Instron testing machine to quantitate bone strength, stiffness, energy absorbed and deformation to failure. The study of test femurs and normal femurs yield the bone strength (load) in pounds and work to failure in joules. Normal femurs exhibit a strength of 96 (±12) pounds. OP-implanted femurs exhibited 35 (±4) pounds, but when corrected for surface area at the site of fracture (due to the "hourglass" shape of the bone defect repair) this correlated closely with normal bone strength. Only one demineralized bone specimen was available for testing with a strength of 25 pounds, but, again, the strength correlated closely with normal bone when ; corrected for fracture surface area.

E. Histomorphometry/Histology

Following biomechanical testing the bones are immediately sliced into two longitudinal sections at the defect site, weighed, and the volume measured. One-half is fixed for standard calcified bone histomorphometrics with fluorescent stain incorporation evaluation, and one-half is fixed for decalcified hemotoxylin/eosin stain histology preparation.

F. Biochemistry

Selected specimens from the bone repair site (n=6) are homogenized in cold 0.15M NaCl, 3 mM NaHCO$_3$, pH 9.0 by a Spex freezer mill. The alkaline phosphatase activity of the supernatant and total calcium content of the acid soluble fraction of sediment are then determined.

G. Histopathology

The final autopsy reports reveal no unusual or pathologic findings noted at necropsy of any of the animals studied. Portion of all major organs are preserved for further study. A histopathological evaluation is performed on samples of the following organs: heart, lung, liver, both kidneys, spleen, both adrenals, lymph nodes, left and right quadriceps muscles at mid-femur (adjacent to defect site in experimental femur). No unusual or pathological lesions are seen in any of the tissues. Mild lesions seen in the quadriceps muscles are compatible with healing responses to the surgical manipulation at the defect site. Pulmonary edema is attributable to the euthanasia procedure. There is no evidence of any general systemic effects or any effects on the specific organs examined.

H. Feline Study Summary

The 1 cm femoral defect cat study demonstrates that devices comprising a matrix containing disposed osteogenic protein can: (1) repair a weight-bearing bone defect in a large animal; (2) consistently induces bone formation shortly following (less than two weeks) implantation; and (3) induce bone by endochondral ossification, with a strength equal to normal bone, on a volume for volume basis. Furthermore, all animals remained healthy during the study and showed no evidence of clinical or histological laboratory reaction to the implanted device. In this bone defect model, there was little or no healing at control bone implant sites. The results provide evidence for the successful use of osteogenic devices to repair large, non-union bone defects.

3. Rabbit Mode:

A. Procedure and Results

Eight mature (less than 10 lbs) New Zealand White rabbits with epiphyseal closure documented by X-ray were studied. The purpose of this study is to establish a model in which there is minimal or no bone growth in the control animals, so that when bone induction is tested, only a strongly inductive substance will yield a positive result. Defects are created in the rabbits, with implantation of: OP (n =5), DBM (n=8), GuHCI-DBM (n=6), and no implant (n=10). Six OP implants are supplied and all control defects have no implant placed.

Of the eight animals (one animal each was sacrificed at one and two weeks), 11 ulnae defects are followed for the full course of the eight week study. In all cases (n=7) following osteo-periosteal bone resection, the no implant animals establish no radiographic union by eight weeks. All no implant animals develop a thin "shell" of bone growing from surrounding bone present at four weeks and, to a slightly greater degree, by eight weeks. In all cases (n=4), radiographic union with marked bone induction is established in the OP-implanted animals by eight weeks. As opposed to the no implant repairs, this bone repair is in the site of the removed bone.

Radiomorphometric analysis reveal 90% OP-implant bone repair and 18% no-implant bone repair at sacrifice at eight weeks. At autopsy, the OP bone appears normal, while "no implant" bone sites have only a soft fibrous tissue with no evidence of cartilage or bone repair in the defect site.

B. Allograft Device

In another experiment, the marrow cavity of the 1.5 cm ulnar defect is packed with activated OP rabbit bone powder and the bones are allografted in an intercalary fashion. The two control ulnae are not healed by eight weeks and reveal the classic "ivory" appearance. In distinct contrast, the OP-treated implants "disappear" radiographically by four weeks with the start of remineralization by six to eight weeks. These allografts heal at each end with mild proliferative bone formation by eight weeks.

This type of device serves to accelerate allograph repair.

B. Summary

These studies of 1.5 cm osteo-periosteal defects in the ulnae of mature rabbits show that: (1) it is a suitable model for the study of bone growth; (2) "no implant" or GuHCl negative control implants yield a small amount of periosteal-type bone, but not medullary or cortical bone growth; (3) OP-implanted rabbits exhibited proliferative bone growth in a fashion highly different from the control groups; (4) initial studies show that the bones exhibit 50% of normal bone strength (100% of normal correlated vol:vol) at only eight weeks after creation of the, surgical defect; and (5) OP-allograft studies reveal a marked effect upon both the allograft and bone healing.

V. SYNTHETIC PROBES, OP GENE DESIGN, AND CLONING STRATEGY

A synthetic concensus gene shown in FIG. 13 is designed as a hybridization probe based on the predictions from homology with an osteogenic protein-related gene family and from human codon bias of the TGF-beta family.

Tryptic peptides derived from BOP and obtained by Edman degradation provide amino acid sequences that showed strong homology with the Drosophila DPP protein sequence (as inferred from the gene), the Xenopus VG1 protein, and somewhat less homology to TGF-beta and inhibin, as demonstrated below in Table 7.

TABLE 7

| protein | amino acid sequence | homology |
|---|---|---|
| (BOP) | DFDAYYCSGACQFPS | (9/15 matches) |
|  | ****** * ** |  |
| (DPP) | GYDAYYCHGKCPFFL |  |
| (BOP) | DFDAYYCSGACQFPS | (6/15 matches) |
|  | * ** * * * |  |
| (Vgl) | GYMANYCYGECPYPL |  |
| (BOP) | DFDAYYCSGACQFPS | (5/15 matches) |
|  | * ** * * |  |
| (inhibin) | GYHANYCEGECPSHI |  |
| (BOP) | DFDAYYCSGACQFPS | (4/15 matches) |
|  | * * * * |  |
| (TGF-Beta) | GYHANFCLGPCPYIW |  |
| (BOP) | K/R—CCVPTELSAISMLYLDEN | (12/20 matches) |
|  | ***** * **** * * |  |
| (Vgl) | LPCCVPTKMSPISMLFYDNN |  |
| (BOP) | K/R—CCVPTELSAISMLYLDEN | (12/20 matches) |
|  | * ***** * **** * |  |
| (inhibin) | KSCCVPTKLRPMSMLYYDDG |  |
| (BOP) | K/R—CCVPTELSAISMLYLDEN | (11/20 matches) |
|  | * ***** * **** |  |
| (DPP) | KACCVPTQLDSVAMLYLNDQ |  |
| (BOP) | K/R—CCVPTELSAISMLYLDEN | (6/20 matches) |
|  | **** * * |  |
| (TGF-beta) | APCCVPQALEPLPIVYYVG |  |
| (BOP) | LYVDF | (5/5 matches) |
|  | ***** |  |
| (DPP) | LYVDF |  |
| (BOP) | LYVDF | (4/5 matches) |
|  | **** * |  |
| (Vgl) | LYVEF |  |
| (BOP) | LYVDF | (4/5 matches) |
|  | ** ** |  |
| (TGF-beta) | LYIDF |  |
| (BOP) | LYVDF | (2/4 matches) |
|  | * * |  |
| (inhibin) | FFVSF |  |

*match

In determining the amino acid sequence of an OP from which the nucleic acid sequence can be determined, the following points are considered: (1) the amino acid sequence determined by Edman degradation of OP tryptic fragments is ranked highest as long as it has a strong signal and shows homology or conservative changes when aligned with the other members of the gene family; (2) where the sequence matches for all four proteins, it is used in the synthetic gene sequence; (3) matching amino acids in DPP and Vgl are used; (4) If Vgl or DPP diverged but either one were matched by TGF-beta or by inhibin, this matched amino acid is chosen; (5) where all sequences diverged, the DPP sequence is initially chosen, with a later plan of creating the Vgl sequence by mutagenesis kept as a possibility. In addition, the consensus sequence is designed to preserve the disulfide crosslinking and the apparent structural homology.

The purpose of the synthetic concensus gene is to serve as a probe and for expression of a consensus protein. Such protein may be expressed in bacteria or other hosts, and may be implanted in an animal model or human. In addition, as more amino acid sequences of OP become available, they can be compared with the gene family discussed in Table 7, and the consensus gene can be improved to match, using known methods of site directed mutagenesis. In the process, a family of analogs can be developed.

Probes may be constructed using conventional techniques comprising a group of sequences of nucleotides which encode any portion of the amino acid sequence of the osteogenic protein produced in accordance with the foregoing isolation procedure. Use of such pools of probes will enable isolation of a DNA encoding the intact protein.

For example, cells known to express the protein are extracted to isolate total cytoplasmic RNA. An oligo-dT column can be used to isolate mRNA. This mRNA can be size fractionated by, for example, gel electrophoresis. The fraction which includes the mRNA of interest may be determined by inducing transient expression in a suitable host cell and testing for the presence of osteogenic protein using, for example, antibody raised against peptides derived from the tryptic fragments of OP in an immunoassay. The mRNA fraction is then reverse transcribed to single stranded cDNA using reverse transcriptase; a second complementary DNA strand can then be synthesized using the cDNA as a template. The double-standard DNA is then ligated into vectors which are used to transfect bacteria to produce a cDNA library.

The radiolabelled consensus sequence, portions thereof, and/or synthetic deoxy oligonucleotides complementary to codons for the known amino acid sequences in the OP may be used to identify which of the DNAs in the cDNA library encode the full length osteogenic protein by standard DNA-DNA hybridization techniques. Alternatively, the DNA sequence encoding the osteogenic protein may be obtained by screening genomic libraries using these probes.

In an alternative strategy, continued sequencing of substantially pure intact OP and its subunits will lead to a complete amino acid sequence of the protein. With this data in hand, synthetic DNAs encoding the protein, and various analogs, muteins, fusion proteins, allelic variants, and other constructs having osteogenic activity can be synthesized readily using, for example, automated oligonucleotide synthesis equipment and assembly of intact genes if necessary.

The invention may be embodied in other specific forms.

What is claimed is:

1. A method for inducing heterotopic bone formation in a mammal comprising:

the step of implanting a biocompatible matrix and a substantially pure osteogenic protein at a heterotopic locus in said mammal, said osteogenic protein comprising a pair of polypeptide chains disulfide bonded to produce a dimeric species having a conformation such that said pair of polypeptide chains is capable of inducing endochondral bone formation in a mammal when implanted with said matrix in a mammal.

2. The method of claim 1 wherein said heterotopic bone formation is contiguous with existing bone.

3. The method of claim 1 for correcting acquired or congenital skeletal anomalies.

4. The method of claim 1 wherein said locus is between weight-bearing bones.

5. The method of claim 1 wherein said matrix comprises close-packed particulate matter having a particle size within the range of 70–850 µm.

6. The method of claim 5 wherein said particulate matter has a particle size within the range of 70–420 µm.

7. The method of claim 1 wherein said matrix comprises a material selected from the group consisting of collagen, hydroxyapatite, tricalcium phosphate, polymers comprising lactic acid monomer units, polymers comprising glycolic acid monomer units, muscle, and mixtures thereof.

8. The method of claim 1 wherein said matrix comprises allogenic bone.

9. The method of claim 1 wherein said matrix comprises demineralized, protein extracted, xenogenic bone.

10. The method of claim 1 wherein said matrix comprises a molded porous solid.

11. The method of claim 1 wherein said osteogenic protein is unglycosylated.

12. The method of claim 1 wherein said osteogenic protein is glycosylated.

13. The method of claim 1 wherein said osteogenic protein has a half maximum activity of at least about 25 to 50 ng per 25 mg of said matrix.

14. The method of claim 11 wherein one chain of said pair of polypeptide chains has average molecular weight of about 14 kD and the other has an average molecular weight of about 14 kD, both determined by comparison to molecular weight standards in SDS-polyacrylamide gel electrophoresis under reducing conditions.

15. The method of claim 12 wherein one chain of said pair of polypeptide chains has an average molecular weight of about 16 kD and the other has an average molecular weight of about 18 kD, both determined by comparison to molecular weight standards in SDS-polyacrylamide gel electrophoresis under reducing conditions.

16. The method of claim 1 wherein said osteogenic protein has the approximate amino acid composition set forth below:

| Amino acid residue | Rel. no. res./molec. | Amino acid residue | Rel. no. res./molec. |
|---|---|---|---|
| Aspartic acid | 22 | Tyrosine | 11 |
| Asparagine | | Valine | 14 |
| Glutamic acid/ | 24 | Methionine | 3 |
| Glutamine | | Cysteine | 16 |
| Serine | 24 | Isoleucine | 15 |
| Glycine | 29 | Leucine | 15 |
| Histidine | 5 | Proline | 14 |
| Arginine | 13 | Phenylalanine | 7 |
| Threonine | 11 | Tryptophan | ND |
| Alanine | 18 | | |
| Lysine | 12 | | |

17. A method of repairing a weight-bearing bone defect in a mammal comprising:
   the step of implanting a biocompatible matrix and a substantially pure osteogenic protein at a weight-bearing bone locus in said mammal,
      said osteogenic protein comprising a pair of polypeptide chains disulfide bonded to produce a dimeric species having a conformation such that said pair of polypeptide chains is capable of inducing endochondral bone formation in a mammal when implanted with said matrix in a mammal.

18. The method of claim 1 wherein said bone formation is contiguous with existing bone.

19. The method of claim 1 for correcting acquired or congenital skeletal anomalies.

20. The method of claim 1 wherein said matrix comprises close-packed particulate matter having a particle size within the range of 70–850 μm.

21. The method of claim 20 wherein said particulate matter has a particle size within the range of 70–420 μm.

22. The method of claim 1 wherein said matrix comprises a material selected from the group consisting of collagen, hydroxyapatite, tricalcium phosphate, polymers comprising lactic acid monomer units, polymers comprising glycolic acid monomer units, muscle, and mixtures thereof.

23. The method of claim 1 wherein said matrix comprises allogenic bone.

24. The method of claim 1 wherein said matrix comprises demineralized, protein extracted, xenogenic bone.

25. The method of claim 1 wherein said matrix comprises a molded porous solid.

26. The method of claim 1 wherein said osteogenic protein is unglycosylated.

27. The method of claim 1 wherein said osteogenic protein is glycosylated.

28. The method of claim 1 wherein said osteogenic protein has a half maximum activity of at least about 25 to 50 ng per 25 mg of said matrix.

29. The method of claim 26 wherein one chain of said pair of polypeptide chains has an average molecular weight of about 14 kD and the other has an average molecular weight of about 16 kD, both determined by comparison to molecular weight standards in SDS-polyacrylamide gel electrophoresis under reducing conditions.

30. The method of claim 27 wherein one chain of said pair of polypeptide chains has an average molecular weight of about 16 kD and the other has an average molecular weight of about 18 kD, both determined by comparison to molecular weight standards in SDS-polyacrylamide gel electrophoresis under reducing conditions.

31. The method of claim 1 wherein said osteogenic protein has the approximate amino acid composition set forth below:

| Amino acid residue | Rel. no. res./molec. | Amino acid residue | Rel. no. res./molec. |
|---|---|---|---|
| Aspartic acid | 22 | Tyrosine | 11 |
| Asparagine | | Valine | 14 |
| Glutamic acid/ | 24 | Methionine | 3 |
| Glutamine | | Cysteine | 16 |
| Serine | 24 | Isoleucine | 15 |
| Glycine | 29 | Leucine | 15 |
| Histidine | 5 | Proline | 14 |
| Arginine | 13 | Phenylalanine | 7 |
| Threonine | 11 | Tryptophan | ND |
| Alanine | 18 | | |
| Lysine | 12 | | |

* * * * *